(12) United States Patent
Gonzalez et al.

(10) Patent No.: US 7,407,929 B2
(45) Date of Patent: Aug. 5, 2008

(54) LEPTIN PEPTIDE ANTAGONISTS

(75) Inventors: Ruben Rene Gonzalez, Watertown, MA (US); Paul C. Leavis, Epping, NH (US)

(73) Assignee: Boston Biomedical Research Institute, Watertown, MA (US)

( * ) Notice: Subject to any disclaimer, the term of this patent is extended or adjusted under 35 U.S.C. 154(b) by 501 days.

(21) Appl. No.: 10/841,218

(22) Filed: May 7, 2004

(65) Prior Publication Data

US 2005/0250690 A1    Nov. 10, 2005

(51) Int. Cl.
*A61K 38/00* (2006.01)
(52) U.S. Cl. .............................. 514/2; 514/12; 530/300
(58) Field of Classification Search .................. None
See application file for complete search history.

(56) References Cited

U.S. PATENT DOCUMENTS

| | | |
|---|---|---|
| 6,399,745 B1 | 6/2002 | Ertl et al. |
| 2002/0160935 A1 | 10/2002 | Cawthorne et al. |
| 2004/0048773 A1 | 3/2004 | Cawthorne et al. |
| 2004/0229783 A1 | 11/2004 | Pothoulakis et al. |

OTHER PUBLICATIONS

Matuuoka et al., Biochem. Biophys. Res. Commun. 256: 480-484, 1999.*
Verploegen et al., FEBS Letters 405, 237-240, 1997.*
Rohner-Jearnrenaud et al., The New Eng. J. Med., 334: 324-325, 1996.*
Campfield et al., Science 280: 1383-1387, 1998.*
Grasso et al., Endocrinol. 138: 1413-1418, 1997.*

* cited by examiner

*Primary Examiner*—Robert S. Landsman
*Assistant Examiner*—Gyan Chandra
(74) *Attorney, Agent, or Firm*—Pierce Atwood LLP; Kevin M. Farrell; David J. Wilson

(57) ABSTRACT

Disclosed herein are peptides comprising a leptin sequence and methods for their use in preventing ObR signaling in a leptin-responsive cell. A leptin peptide of the present invention binds to but does not activate ObR signaling in a leptin-responsive cell, thereby inhibiting the up-regulatory effects of leptin on ObR signaling in the leptin-responsive cell. Administration of the peptide effectively prevents embryo implantation in a mammal to which the peptide has been administered. Also disclosed herein is a method for identifying a peptide antagonist of ObR, wherein the peptide comprises a leptin sequence.

7 Claims, 15 Drawing Sheets

Fig 11. Impairment of mouse embryo implantation by intra-uterine injection of OB-R inhibitors

SEQUENCE LISTING

```
<160> NUMBER OF SEQ ID NOS: 3

<210> SEQ ID NO 1
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Gln Lys Val Gln Asp Asp Thr Lys Thr Leu Ile Lys Thr Ile Val
 1               5                  10                  15

Thr Arg Ile Asn Asp Ile Ser His Thr Gln Ser Val Ser Ser Lys Gln
            20                  25                  30

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Arg Asn Val Ile Gln Ile Ser Asn Asp Leu Glu Asn Leu Arg Asp
 1               5                  10                  15

Leu Leu His Val Leu Ala Phe Ser Lys Ser
            20                  25
```

```
<210> SEQ ID NO 3
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Ala Glu Val Leu Asn Arg Ser Asp Leu Ile Gln Arg Ile Ser Phe
 1               5                  10                  15

Ser Leu Asp Leu Asn Asn Ser Lys Leu His
             20                  25
```

LEPTIN PEPTIDE ANTAGONISTS

BACKGROUND OF THE INVENTION

Leptin (OB, the product of ob gene), is a pleiotropic molecule mainly secreted by white adipocytes that plays a relevant role in the regulation of body weight and food intake (for Review see Gonzalez et al., 2000). In contrast to leptin, the leptin receptor (OB-R, the product of the db gene) has several spliced variants. The full-length and functional OB-R (OB-Rb) is expressed by the hypothalamus and plays a key role in the energy balance process (Tartaglia et al., 1995). OB-R isoforms with shorter cytoplasmatic tail are expressed in many tissues, but their function remain unknown (Wang et al., *J. Biol. Chem*, 272: 16216-16223 (1997)). A soluble OB-R that could regulate leptin biological actions has been also described (Lewandowski et al., *J. Clin. Endocrinol. Metab.* 84: 300-306 (1999)). Leptin sequence is highly conserved in many species but some differences in OB-R sequences are found between species.

Binding of leptin to OB-R induces the homodimerization of the receptor that in turns allow the binding of Janus kinase 2 (JAK2) to specific box motifs in the intracytoplasmatic tail of OB-R. JAK2 phosphorylates OB-R followed by phosphorylation of signal transducer and activator of transcription 3 (STAT3), which, in turn dimerizes and translocates to the nucleus, thus activating several downstream signaling pathways. In addition to the JAK-STAT signaling pathway, other pathways, including the mitogen-activated protein kinase (MAPK), protein kinase C(PKC), and PI3-kinase pathways, are also activated by leptin (Ghilardi et al., *Proc. Natl. Acad. Sci. USA* 93: 6231-6235 (1996); Zabeau et al., *FEBS Lett.* 546: 45-50 (2003)).

Since the discovery of leptin 10 years ago (Zhang et al., 1994) emerging evidence have been accumulating that strongly link leptin signaling with the reproductive function (for review see Gonzalez et al., 2000; Castracane and Henson, *Semin. Reprod. Med.* 20(2): 89-92 (2002)).

In vitro studies have shown that leptin and OB-Rb are expressed by female reproductive tissues, including ovaries (Cioffi et al., *Mol. Hum. Reprod.* 3: 467-472 (1997); Zachow et al., *Endocrinol.* 138: 847-850 (1997); Agarwal et al., *J. Clin. Endocrinol. Metab.* 84: 1072-1076 (1999)), oocytes, preimplantation embryo (Matsuoka et al., *Biochem. Byophys. Res. Commun.*, 256: 480-484 (1999); Kawamura et al., *Endocrinology* 143: 1922-1931 (2002)), endometrium (Gonzalez et al, 2000; Wu et al., *Mol. Hum. Reprod.* 8: 456-464 (2002)) and placenta (Masuzaki et al., *Nat. Med.* 3: 1029-1033 (1997); Senaris et al., *Endocrinol.* 138: 4501-4504 (1997)). Leptin can promote the development of mouse preimplantation embryos through OB-R signaling (Kawamura et al., *Endocrinology* 143: 1922-1931 (2002)). Leptin protein has been found in human and mouse oocytes, and preimplantation embryos (Cioffi et al., *Mol. Hum. Reprod.* 3: 467-472 (1997); Antczak and Van Blerkom, *Mol. Hum. Reprod.* 3: 1067-1086 (1997)). But, leptin mRNA has been only found at blastocyst stage. Leptin at physiological concentrations could positively affect phosphorylation of STAT3 (p-STAT3) in mouse oocytes (Matsuoka et al., *Biochem. Biophys. Res. Commun.* 256: 480-484 (1999)). These data suggest that OB-R signaling in oocytes and early preimplantation embryos up to morula stage would require maternal supply of leptin (Kawamura et al., *Endocrinology* 143: 1922-1931 (2002)). A particular cell-borne pattern for leptin and STAT3 has been found in outer blastomers of human and mouse blastocysts (Antczak and Van Blerkom, *Mol. Hum. Reprod.* 3: 1067-1086 (1997)). These data would indicate that leptin/ OB-R are required to establish the cross-talk between the implanting embryo and the receptive endometrium.

In vitro the secretion of leptin is regulated by human preimplantation embryos co-cultured with endometrial cells (Gonzalez et al., 2000). Leptin induces the acquisition of the invasive phenotype of human trophoblast cells (Castellucci et al., *Mol. Hum. Reprod.* 6(10): 951-8 (2000); Gonzalez et al., *Early Preg. Biol. Med.* 5: 132-143 (2001)). Leptin increase the levels of β3-integrin (a marker of endometrial receptivity) in human endometrial epithelial cells (Gonzalez and Leavis, 2001). Moreover, leptin in a dose-dependent manner increased p-STAT3 and leukemia inhibitory factor (LIF), interleukin-1 (IL-1) and levels of their cognate receptors in rabbit (Gonzalez and Leavis, 2003) and human endometrial cells (Gonzalez et al., 2004). Lastly, blockade of the OB-R with antibodies abrogated leptin-induced effects suggesting that leptin signaled through OB-R and the JAK/STAT3 pathways (Gonzalez et al 2003; Gonzalez et al., 2004).

Although the specific mechanisms whereby leptin modulates reproductive function are not completely understood leptin appears to be essential for normal preimplantation and/ or implantation processes. Overall in vitro and in vivo data suggest that leptin signaling impact implantation capabilities in both entities: preimplantation embryo and endometrium.

In vivo studies have shown that mouse mutant deficient in leptin (ob/ob) (Zhang et al., 1994) or OB-R (db/db) are obese and infertile. Fertility can be restored in ob/ob by exogenous leptin (Chehab et al., *Nat Genet.* 12: 318-320 (1996)). The withdrawal of leptin infusion in ob/ob females short after fertilization impairs implantation (Malik et al., *Endocrinology* 142: 5198-5202 (2001)). Leptin injection into starved mice restores fertility (Ahima et al., *Nature* 382: 250-252 (1996)). A postovulatory increase in serum leptin concentration appears to be associated with implantation potential (Cioffi et al., *Mol. Hum. Reprod.* 3: 467472 (1997)) and low expression of OB-R has been found in endometrium from women with unexplained infertility (Alfer et al., *Mol. Hum. Reprod.* 6: 595-601 (2000)). These data suggest that in vivo leptin could act in an autocrine or paracrine manner to regulate biological functions that may mediate the implantation process.

From the analysis of a structural- based model for leptin/ OB-R complex the helices I and III of leptin are likely the interacting regions for its binding to OB-R (Gonzalez and Leavis, 2003). In consequence, a peptide (LPA-2) derived from helix III of leptin is able to inhibit leptin binding to its receptor in vitro. Moreover, LPA-2 interferes with the leptin signaling pathways responsible for leptin-induced increase in levels of IL-1, LIF and β3-integrin by rabbit and human endometrial cell cultures (Gonzalez and Leavis, 2003; Gonzalez et al., 2004).

These data suggest that targeting the leptin receptor may negatively affect implantation. Therefore, it was hypothesized that the inhibition of OB-R function (in endometrium and/or preimplantation embryos) by LPA-2 or anti mouse OB-R antibodies will impair mouse embryo implantation. In the present study, the impact of the intrauterine injection of LPA-2 and anti-OB-R antibodies at Day 3 of pregnancy in a mouse model was investigated. Both OB-R inhibitors impaired mouse implantation and affected the endometrial expression of several molecules related to the implantation potential. Overall, our results suggest that leptin could be one of the primary factors that initiates and regulates the cascade system of molecules that promote the development of endometrial receptivity and successful implantation.

SUMMARY OF THE INVENTION

The present invention provides peptide compositions, each composition comprising a leptin sequence and characterized by the ability to bind to but not activate the leptin receptor. The specific peptides disclosed, termed LPA-1 and LPA-2, comprise sequence derived from helix I and helix III, respectively, of the human leptin sequence. A peptide of the present invention may be used to alter leptin-dependent functions in leptin-responsive cells.

The present invention provides a method for preventing ObR signaling in a leptin-responsive cell. The method comprises contacting a leptin-responsive cell with a peptide comprising a leptin sequence. A peptide of the present invention comprising a leptin sequence is characterized by its ability to inhibit the up-regulatory effects of leptin on ObR signaling in the leptin-responsive cell. In the present invention, inhibition in the leptin-responsive cell is relative to an identical leptin-responsive cell which has not been contacted with the peptide.

In the present invention, contact of the leptin-responsive cell with a peptide comprising a leptin sequence may be in vitro or in vivo. The cell may be a human or rabbit cell, and may further be an endometrial or other leptin-responsive cell. In the context of the present invention, the endometrial cell may be of epithelial or stromal cell types. A peptide of the present invention is to be delivered in an amount effective to bind but not activate ObR in cells where inhibition of ObR signaling is desirable.

A peptide of the present invention may be administered to a mammal to alter any leptin-dependent function in the mammal. In a preferred embodiment, administration of the peptide results in the prevention of embryo implantation in the mammal. Administration of a peptide comprising a leptin sequence in the present invention may be to any mammal including a human, mouse, or rabbit.

A method for preventing ObR signaling in a leptin-responsive cell may comprise inhibiting the up-regulatory effects of leptin on a signaling event downstream of ObR. The signaling event downstream of the leptin receptor may be p-Stat-3, β3-integrin, IL-1 and/or LIF signaling. The inhibition of ObR signaling may result in an inhibition of the up-regulatory effects of leptin on the expression of a leptin-sensitive target. The leptin-sensitive target may be p-Stat-3, β3-integrin, IL-1R tI, LIF-R, LIF, IL-1β, and/or IL-1Ra.

Also provided herein is a method for identifying a peptide antagonist of ObR wherein the peptide antagonist of ObR comprises a leptin sequence. The method comprises first providing a leptin or leptin equivalent sequence. The method further comprises superimposing the three-dimensional structure of the provided leptin or leptin equivalent sequence on the three-dimensional structure of the G-CSF/G-CSF R complex. The method further comprises identifying a region of the provided leptin or leptin equivalent sequence which superimposes on the residues of G-CSF that interact with G-CSF R in a G-CSF/G-CSF R three-dimensional structure. The method further comprises synthesizing a peptide comprising a leptin or leptin equivalent sequence which corresponds to the identified leptin or leptin equivalent region and testing the peptide in cell culture for its ability to inhibit the up-regulatory effects of leptin on ObR signaling in a leptin-responsive cell. In a preferred embodiment, a leptin region identified in this method may comprise helix I or helix III of the leptin sequence.

value of equal to or less than 0.05 when comparing levels in response to treatments to that of the non-treated controls.

Figure 4:
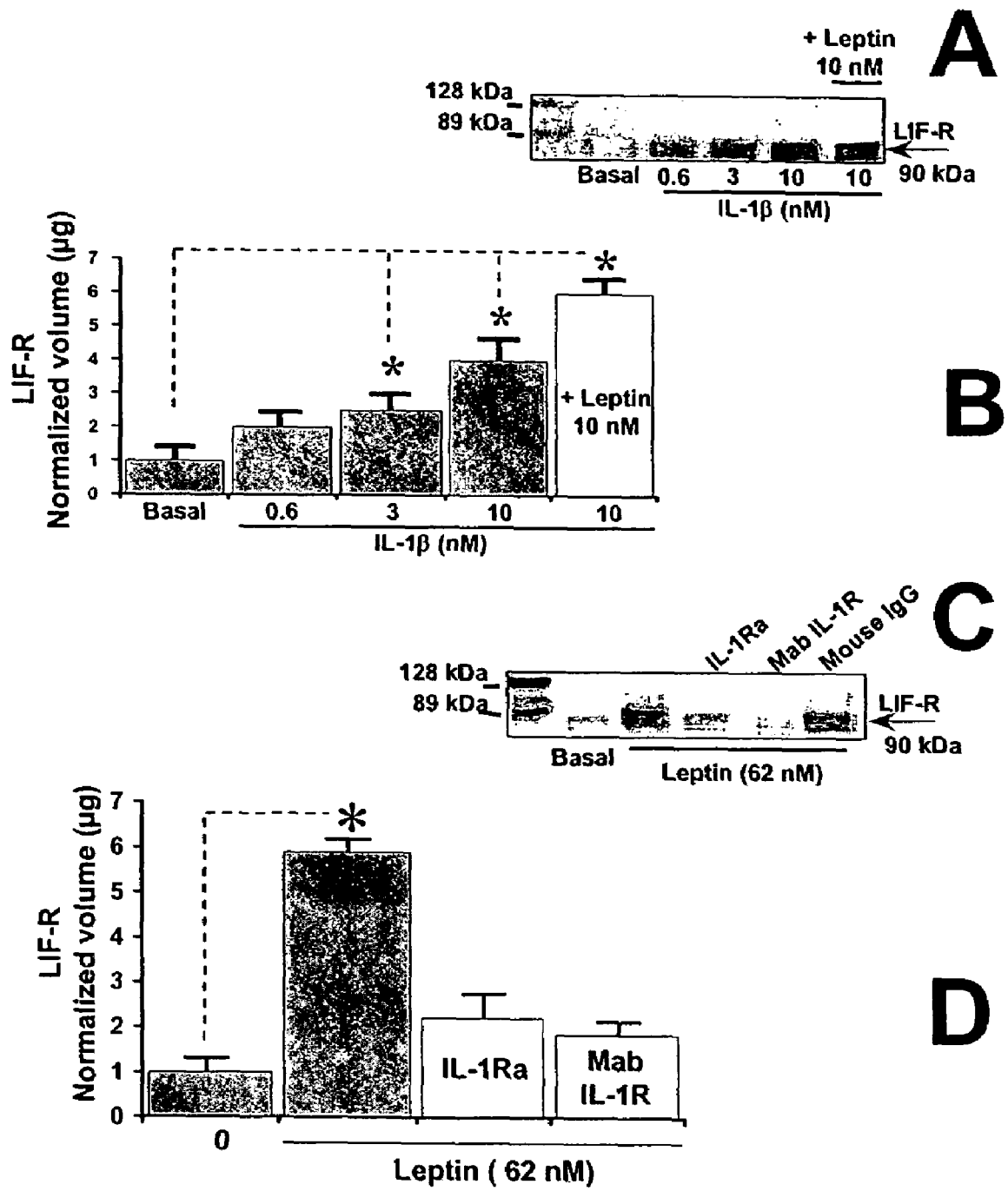

FIG. 4 shows leptin and IL-1 induced LIF-R expression by human endometrial cells are partially blocked by IL-1R tI inhibitors. (A) Representative Western blot of IL-1β induced treatment effects on LIF-R levels in Ishikawa cells in the presence or absence of leptin. (B) Quantitative analysis of IL-1 induced treatment effects on LIF-R levels in Ishikawa cells. (C) Representative Western blot of LIF-R levels following treatment with or without leptin in the presence or absence of IL-1Ra (1000 pg/ml), monoclonal antibody anti IL-1R tI (20 μg/ml) or mouse IgG by Ishikawa cells. (D) The impact of IL-1R tI inhibitors on leptin-mediated LIF-R levels in Ishikawa cells was determined by densitometric analyses. All data was derived from a minimum of three independent experiments using different cell preparations. The results are presented in the graphs are the mean and SE. * denotes a p value of equal to or less than 0.05 when comparing levels in response to treatments to that of the non-treated controls.

Figure 5:
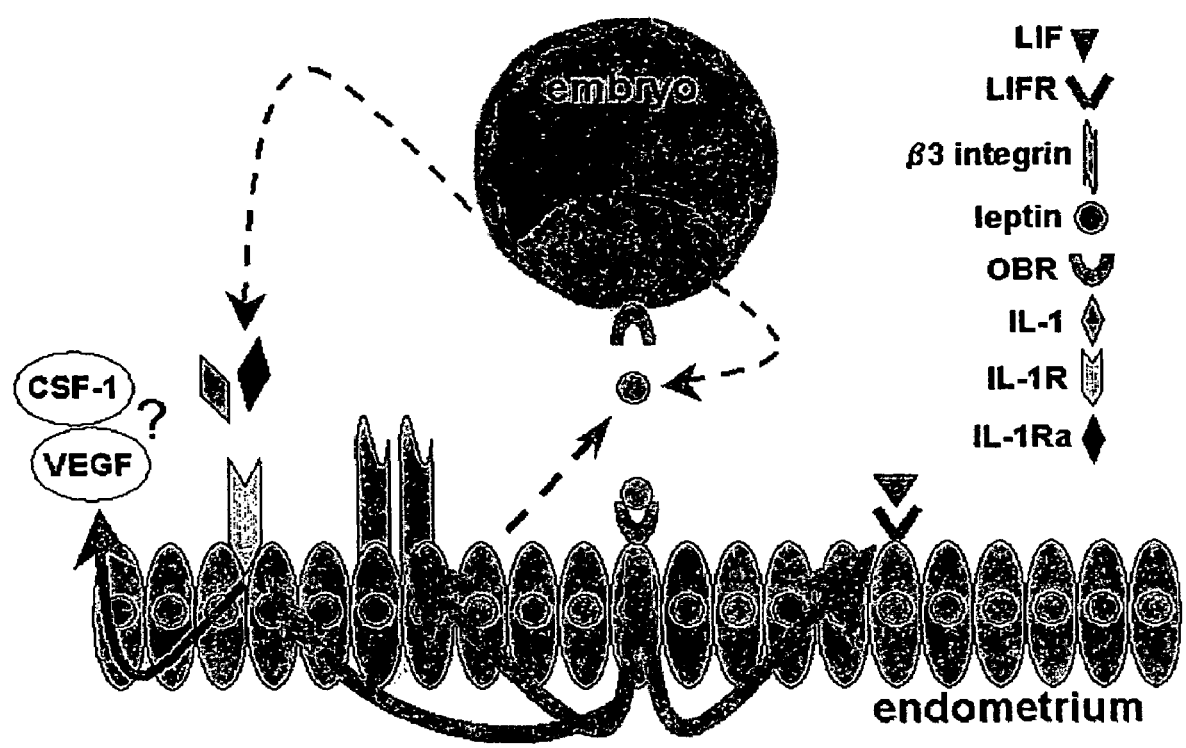

FIG. 5 illustrates a schematic representation of leptin interactions with important factors for implantation. At the time of implantation, leptin secreted by the embryo and/or endometrium (Gonzalez et al., *J. Clin. Endocrinol. Metab.* 85: 4883-4488 (2000)) induces the expression of IL-1 (ligand, receptor and receptor antagonist) (Gonzalez et al., *Mol. Hum. Reprod.* 9: 151-158 (2003)). Leptin directly or indirectly via IL-1 induces the expression of LIF (ligand and receptor) and β3-integrin (a marker for endometrial receptivity) (Gonzalez and Leavis, *Endocrine* 16: 21-28 (2001)). IL-1 could also induce the expression of colony stimulatory factor −1 (CSF-1) (Harty and Kauma, *J. Clin. Endocrinol. Metab.* 75: 947-950 (1992)) and vascular endothelial growth factor (VEGF) (Lebovic et al., *Mol. Hum. Reprod.* 6: 269-275 (2000)). Leptin could be one of the primary factors that initiate and regulate the cascade system of molecules that promote the development of endometrial receptivity and successful implantation.

Figure 6:
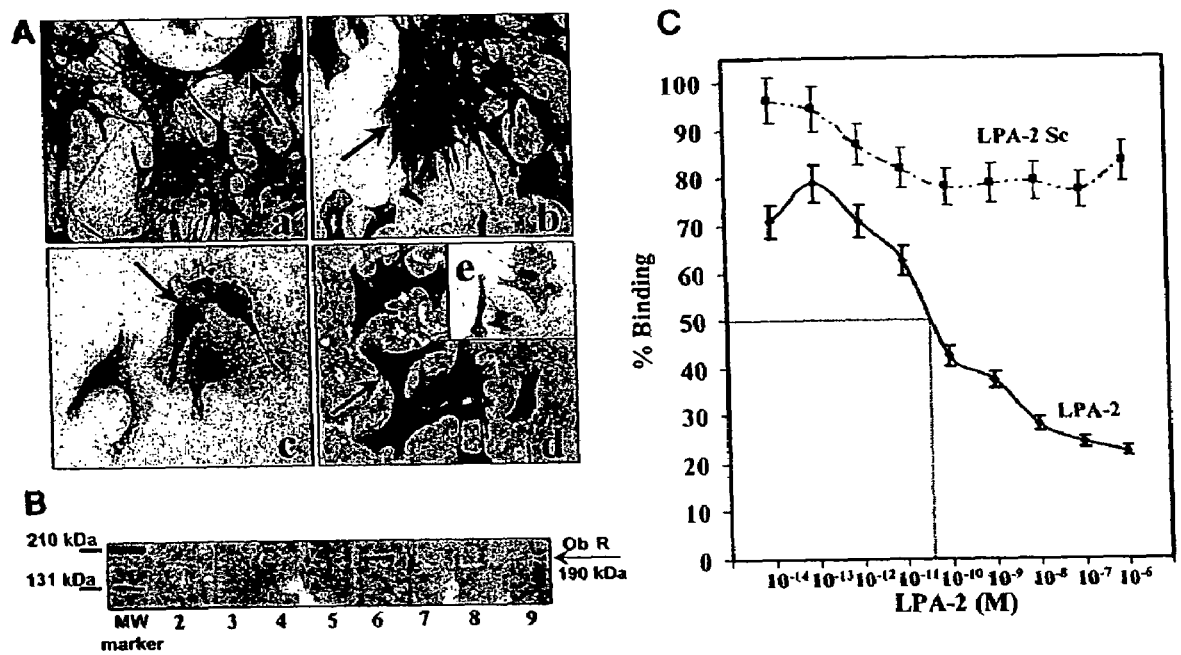

FIG. 6 shows differential expression of vimentin, cytokeratin and OB-R by rabbit endometrial stromal (rESC) and epithelial cells (rEEC). LPA-2 binds to OB-R in rabbit endometrial cells. (A) Immunocytochemical results for the expression of various antigens in rabbit endometrial cells. (Aa) Expression of vimentin was found only in rESC cultures. (Ab) rESC express OB-R. (Ac) Expression of cytokeratin was found only in rEEC cultures (Ad) rEEC also express OB-R. (Ae) The cells were incubated with non-specific species matched IgGs to primary antibodies (negative control). Expression of OB-R was not changed in any cell type by effects of leptin or LPA-2 (data not shown). Arrows indicate positive staining for the different antigens tested. B) Western blot determination of OB-R expression by rabbit endometrial cell cultured in medium containing leptin or LPA-2. rESC: (1) MW marker, (2) Basal medium, (3) leptin (3 nM), (4) LPA-2 (300 nM), (5) Leptin (3 nM) plus LPA-2 (300 nM). rEEC: (6) Basal medium, (7) leptin (3 nM), (8) LPA-2 (300 nM), (9) Leptin (3 nM) plus LPA-2 (300 nM). A 190 kDa band corresponding to the OB-R monomer (long form of functional OB R) was detected in all samples. In addition, several bands corresponding to OB-R isoforms with lower MW were detected. However, neither the treatment with leptin or LPA-2 changes the expression of the OB-R isoforms. C) LPA-2 but not its scrambled version (LPA-2Sc) competes with $^{125}$I-leptin for binding to OB-R in protein extracts from endometrial rabbit cells. LPA-2 binds with high affinity to OB-R (Ki~$0.6\times10^{-10}$ M) expressed by rabbit endometrial cells (rEEC and rESC).

Figure 7:
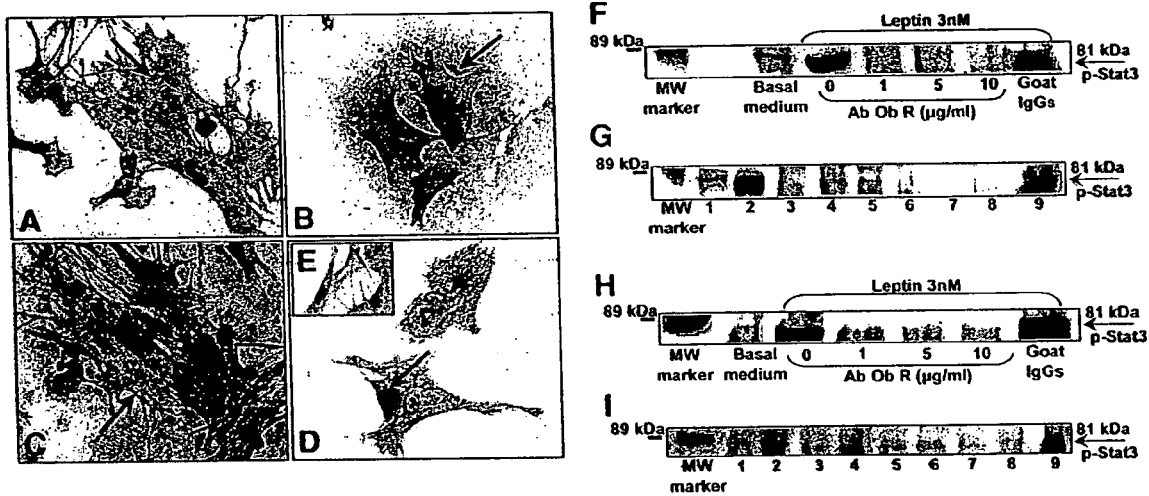

FIG. 7 shows inhibition of leptin up-regulation of p-Stat3 expression in rabbit endometrial cells by an anti-OB-R antibody and LPA-2. (A-E) Immunocytochemical results from the expression of p-Stat3 by rabbit endometrial stromal cells (rESC) cultured in medium containing leptin, LPA-2 or LPA-2Sc (A-E). (A) Basal expression of p-Stat3. (B) pStat3 up-regulation by leptin (3 nM). (C) LPA-2Sc did not affect the leptin up-regulation of p-Stat3. (D) In contrast, LPA-2 significantly inhibits the leptin up-regulation of p-Stat3. (E) Negative control using non-specific species matched IgGs to primary antibodies. Arrows indicate positive staining for the different antigen tested. (F-I) Western blot analysis of the leptin up-regulation of p-Stat3 expression and inhibition of this leptin effect by an anti-OB-R antibody (1-10 μg/ml) and LPA-2 (3-300 nM) in rESC and rabbit endometrial epithelial cells (rEEC). (F) rESC: Inhibition of the leptin up regulation of p-Stat3 in rESC by anti OB-R antibodies. (G) rESC: Inhibition of the leptin up regulation of p-Stat3 in rESC by LPA-2. (1) Basal medium; (2) Leptin (3 nM); (3) LPA-2 (3 nM); (4) Leptin (3 nM) plus LPA-2 (3 nM); (5) LPA-2 (30 nM); (6) Leptin (3 nM) plus LPA-2 (30 nM); (7) LPA-2 (300 nM); (8) Leptin (3 nM) plus LPA-2 (300 nM) and (9) Leptin (3 nM) plus LPA-2Sc (300 nM). (H) rEEC: Inhibition of the leptin up regulation of p-Stat3 in rESC by anti OB-R antibodies. Leptin up-regulated p-Stat3 expression. (I) rEEC: Inhibition of the leptin up-regulation of p-Stat3 in rESC by LPA-2. (1) Basal medium; (2) Leptin (3 nM); (3) LPA-2 (3 nM); (4) Leptin (3 nM) plus LPA-2 (3 nM); (5) LPA-2 (30 nM); (6) Leptin (3 nM) plus LPA-2 (30 nM); (7) LPA-2 (300 nM); (8) Leptin (3 nM) plus LPA-2 (300 nM) and (9) Leptin (3 nM) plus LPA-2Sc (300 nM). Endometrial cells were cultured for 24 h in basal medium alone or containing leptin, anti-OB-R antibody or LPA-2. Negative control includes the cells cultured in medium containing leptin (3 nM) plus 10 μg/ml of non specific goat IgGs or leptin (3 nM) plus LPA-2Sc (300 nM). P-Stat3 (81 kDa band) was detected by western blot.

Figure 8:
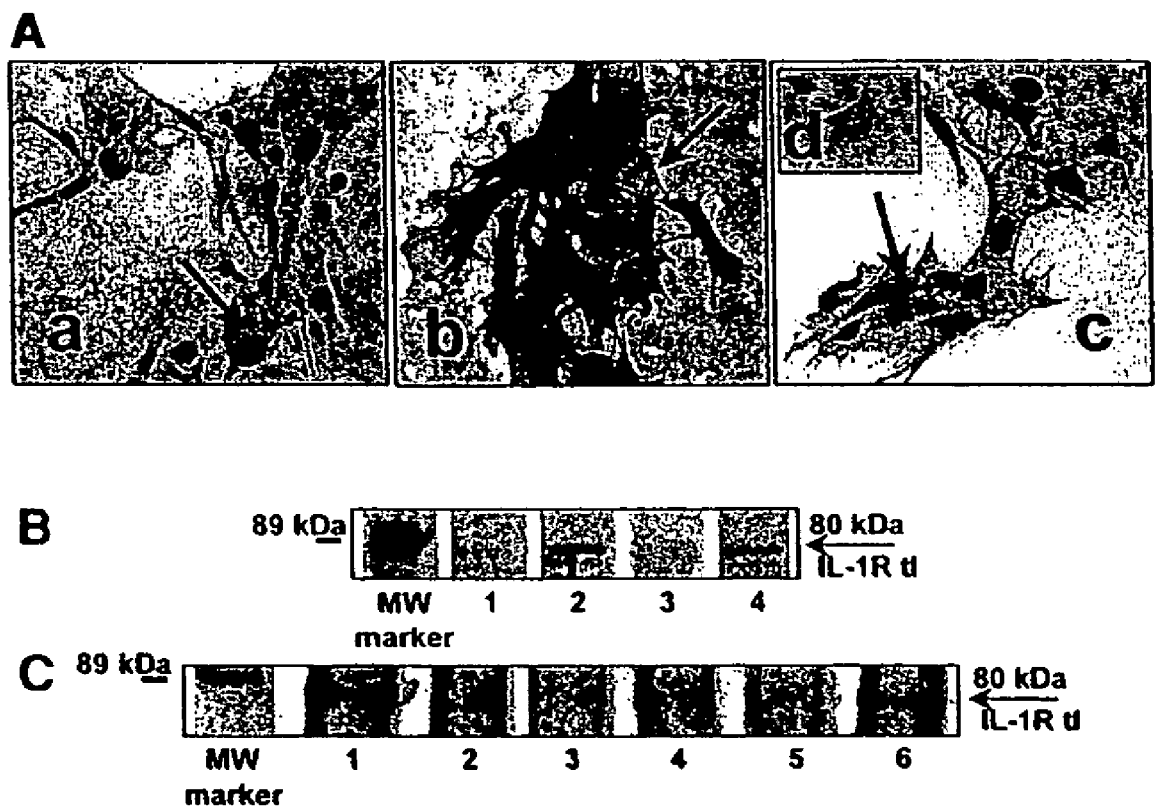

FIG. 8 shows leptin up regulation of IL-1R tI by rabbit endometrial stromal cells (rESC). Inhibition of leptin effects by an anti-OB-R antibody and LPA-2. (A) Immunocytochemical results from the expression of IL-1R tI (Aa) Basal expression of IL-1R tI. (Ab) IL-1R tI up-regulation by leptin (3 nM). (Ac) LPA-2 significantly inhibits the leptin up regulation of IL-1R tI. (Ad) Negative control using non-specific mouse IgGs. Arrows indicate positive staining for IL-1R tI. (B) Western blot analysis of the effects of leptin and anti OB-R antibody on IL-1R tI-expression by rESC. (1) Basal medium; (2) leptin (3 nM); (3) leptin (3 nM) plus anti-OB-R antibody (20 μg/ml), (4) Leptin (3 nM) plus non-specific mouse IgGs (20 μg/ml). (C) Western blot analysis of the effects of leptin and LPA-2 on the IL-1R tI expression by rESC. (1) Leptin (3 nM), (2) Basal medium; (3) LPA-2 (120 nM); (4) Leptin (3 nM) plus LPA-2 (30 nM); (5) Leptin (3 nM) plus LPA-2 (120 nM) and (6) Leptin (3 nM) plus LPA-2Sc (120 nM). Endometrial cells were cultured for 24 h in basal medium alone or containing leptin, anti-OB-R antibody or LPA-2. Negative control includes the cells cultured in medium containing leptin (3 nM) plus 20 μg/ml of non-specific goat IgGs or leptin (3 nM) plus LPA-2Sc (300 nM). IL-1R tI (80 kDa band) was detected by western blot using a specific monoclonal antibody (R&D System). Incubation of rESC with non-specific IgGs or LPA-2Sc did not prevent the leptin up-regulation of IL-1R tI. Similar results were obtained with rabbit endometrial epithelial cells (rEEC).

Figure 9:
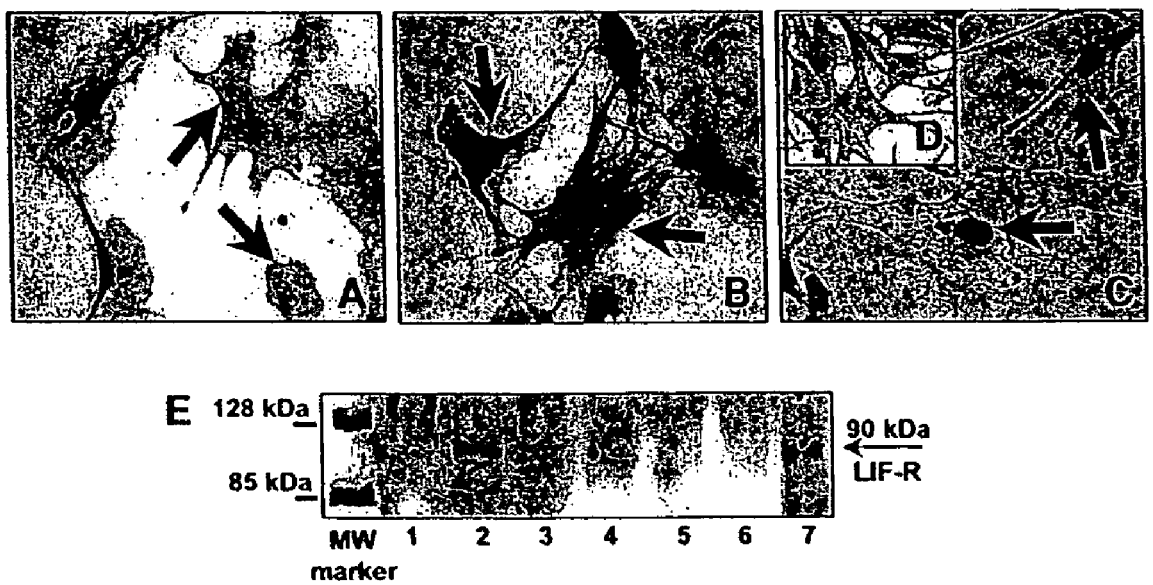

FIG. 9 shows leptin up-regulation of LIF-R by rabbit endometrial cells. Inhibition of leptin effects by an anti OB-R antibody and LPA-2. Immunocytochemical results from the expression of LIF-R (A) Basal expression of LIF-R in rabbit endometrial stromal cells (rESC). (B) LIF-R up-regulation by leptin (3 nM). (C) LPA-2 significantly inhibits the leptin up-regulation of LIF-R. (D) Negative control using non-specific goat IgGs. Arrows indicate positive staining for LIF-R. Similar results were found in rabbit endometrial epithelial cells (rEEC). (E) Western blot analysis of the effects of leptin, anti OB-R antibody and LPA-2 on LIF-R expression by rEEC. (1) Basal medium; (2) leptin (3 nM); (3) leptin (3 nM) plus anti-OB-R antibody (20 μg/ml), (4) Leptin (3 nM) plus non-specific goat IgGs (20 μg/ml), (5) Leptin (3 nM) plus LPA-2 (3 nM), (6) Leptin (3 nM) plus LPA-2 (30 nM) and (7) Leptin (3 nM) plus LPA-2Sc (300 nM). Endometrial cells were cultured for 1 h in basal medium alone or containing leptin, anti-OB-R antibody or LPA-2. Negative control includes the cells cultured in medium containing leptin (3 nM) plus 20 μg/ml of non-specific goat IgGs or leptin (3 nM) plus LPA-2Sc (300 nM). LIF-R (90 kDa band) was detected by Western blot using a specific monoclonal antibody (R & D System). Incubation of rabbit endometrial cells with non-specific IgGs or LPA-2Sc did not prevent the leptin up-regulation of LIF-R.

Figure 10:
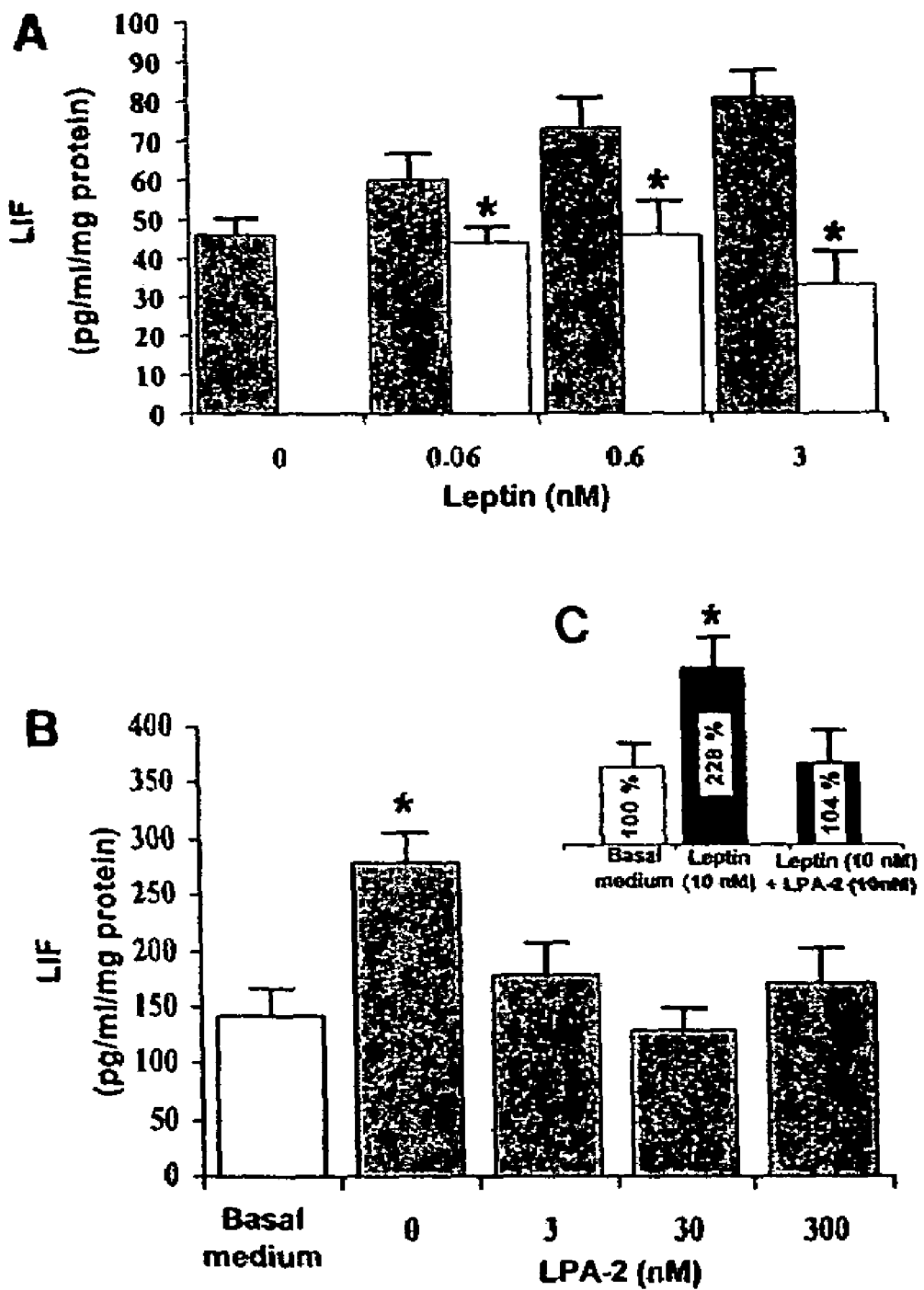

FIG. 10 shows leptin regulation of LIF secretion by rabbit endometrial epithelial cells (rEEC). Inhibition of leptin effects by an anti-OB-R antibody and LPA-2. A) Basal secretion of LIF by rEEC is up-regulated in a dose-response manner by leptin (filled bars) and the addition of the OB-R antibody (20 μg/ml) blocks this leptin effect (empty bars). B) The up-regulation of LIF secretion by leptin (3 nM) is effectively inhibited by LPA-2 (3-300 nM). C) Higher dose of leptin (10 nM) provoked a significant increase of LIF secretion (more than 2-fold) by rEEC cultures. However, the addition of LPA-2 (10 nM) completely inhibited the leptin up-regulatory effects on leptin induced LIF secretion by rEEC. *$P<0.05$.

Figure 11:
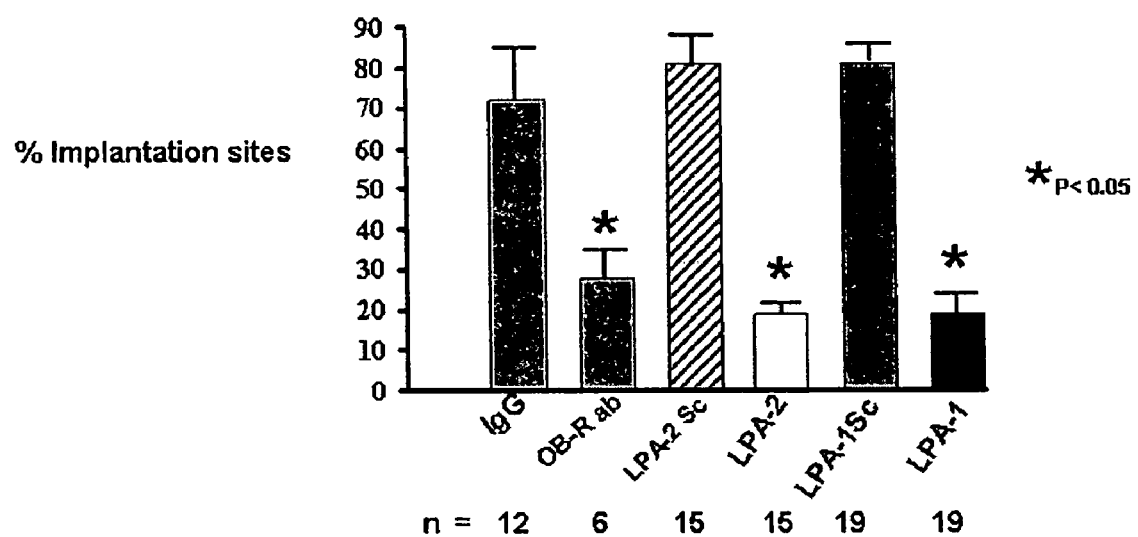

FIG. 11 illustrates the impairment of mouse embryo implantation by intra-uterine injection of OB-R inhibitors.

Figure 12:
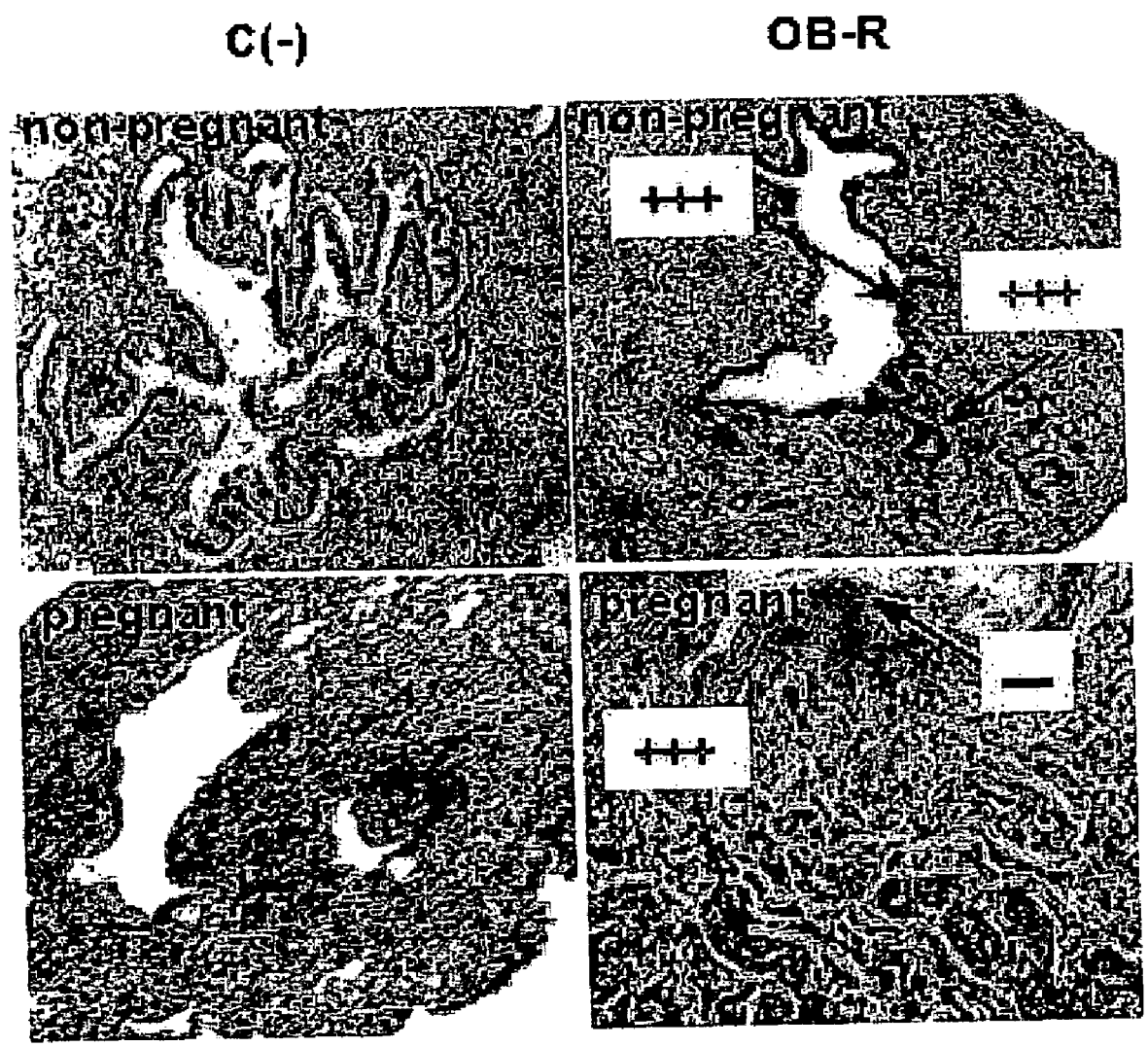

FIG. 12 shows that Ob-R is expressed only in the luminal epithelial cells before implantation occurs. Immunohistochemical determination of OB-R in endometrial sections of pregnant and non-pregnant mice.

Figure 13:
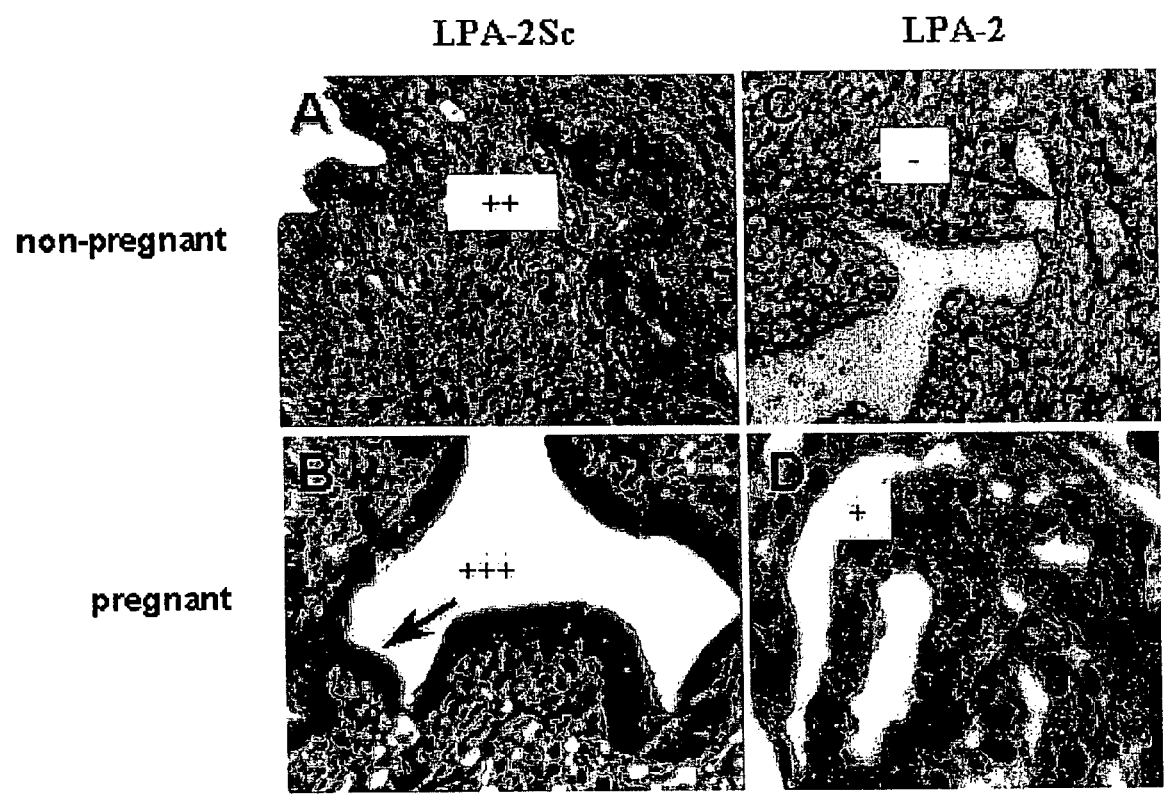

FIG. 13 illustrates that LPA-2 decreases the levels of LIFR in mouse endometrium. Immunohistochemical determination of LIF-R in mouse endometrium in LPA-2-treated pregnant and non-pregnant mice.

Figure 14:
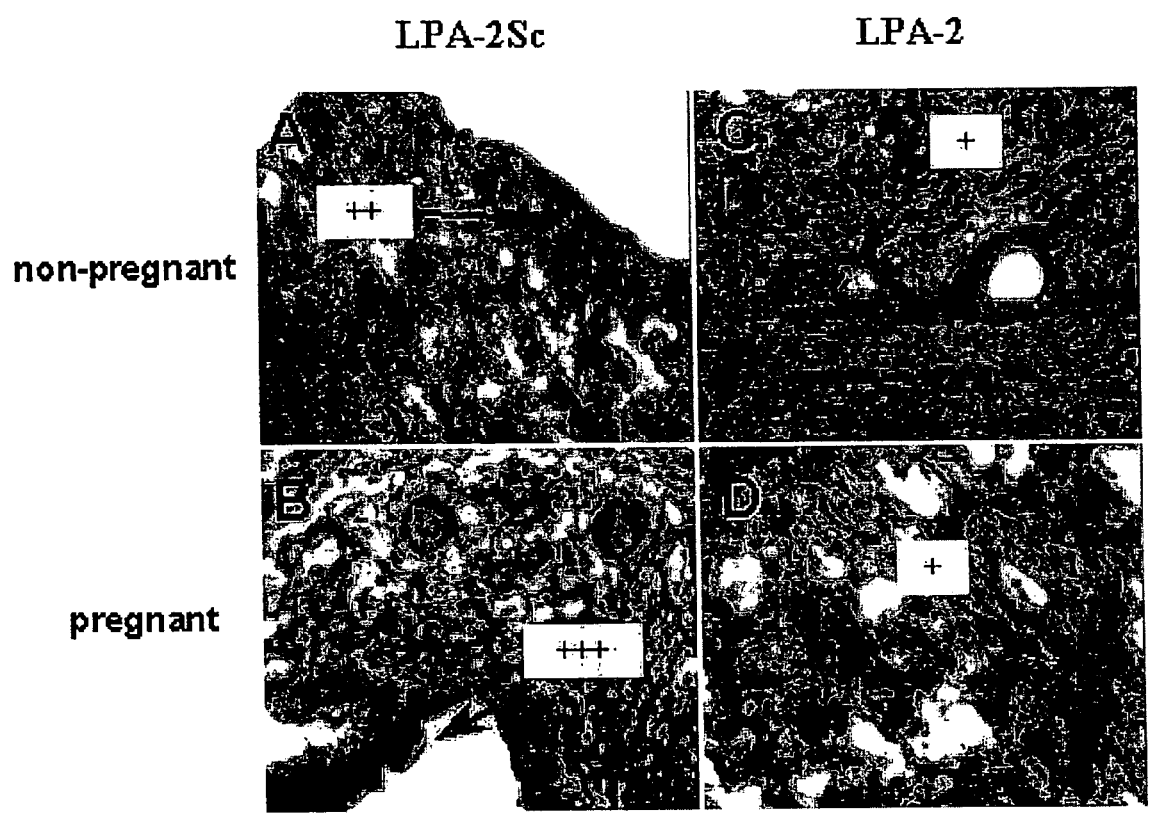

FIG. 14 illustrates that LPA-2 decreases the levels of IL-1R tI in mouse endometrium. Immunohistochemical determination of IL-1R tI in mouse endometrium in LPA-2-treated pregnant and non-pregnant mice.

Figure 15:
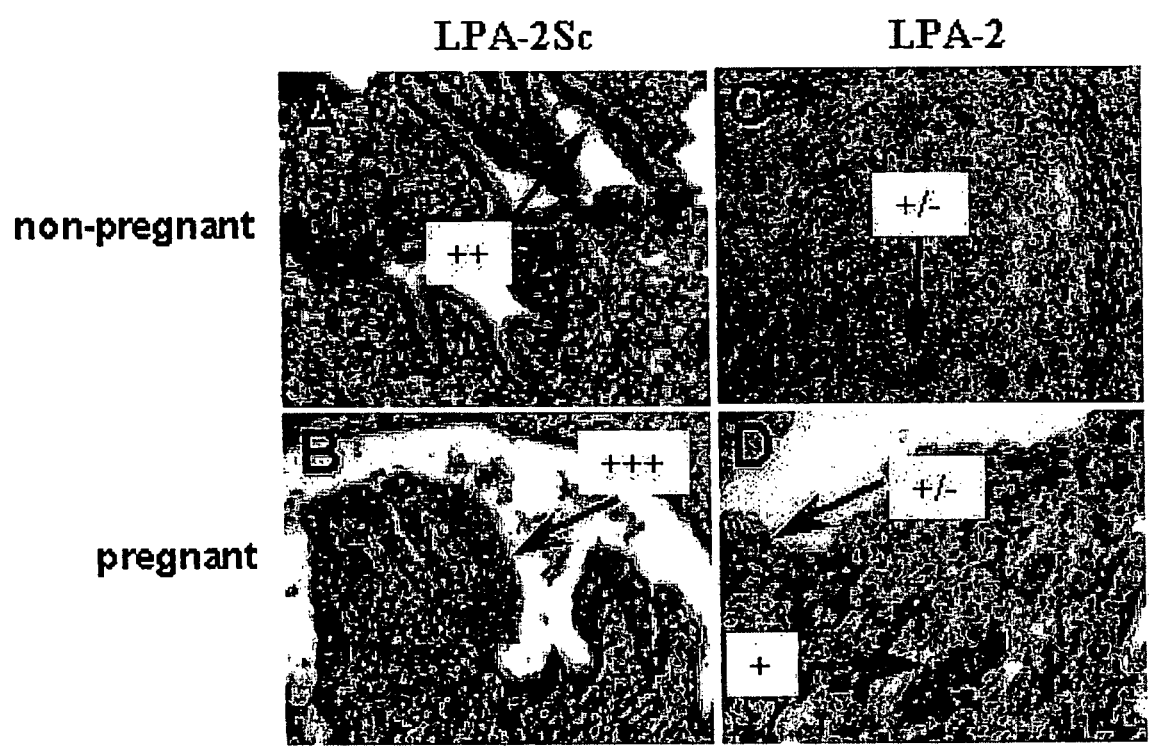

FIG. 15 shows that LPA-2 decreases the levels of β3-integrin in mouse endometrium. Immunohistochemical determination β3-integrin in mouse endometrium in LPA-2-treated pregnant and non-pregnant mice.

DETAILED DESCRIPTION OF THE PRESENT INVENTION

The present invention is based on the finding that peptides comprising a leptin sequence are capable of regulating leptin receptor (Ob-R) function. More specifically, the invention is based on the observation that peptides comprising a leptin sequence bind to the leptin receptor and blocks its activation. Such peptides may be utilized in controlling leptin-dependent functions, including but not limited to embryo implantation. The leptin sequence can be further exploited in identifying other peptides which act as potent inhibitors of leptin receptor function.

The present invention relates to methods and compositions for inhibiting Ob-R signaling in a leptin-responsive cell. More specifically, the present invention relates to methods and compositions for inhibiting Ob-R signaling in a leptin-responsive cell comprising contacting the leptin-responsive cell with a peptide comprising a leptin sequence. In embodiments of the present invention, the peptide comprising a leptin sequence acts as an antagonist of Ob-R in the leptin-responsive cell. The peptide competes with the native leptin ligand for binding to its receptor, or alternatively displaces the native leptin ligand from an already bound receptor. As exemplified, a peptide of the present invention binds Ob-R with high affinity and specificity. A peptide for use in the methods of the present invention inhibits the up-regulatory effects of leptin on Ob-R signaling in the leptin-responsive cell, the leptin-responsive cell being relative to an identical leptin-responsive cell which has not been contacted with the peptide.

Methods disclosed herein for inhibiting Ob-R signaling in a leptin-responsive cell may be carried out in vitro. Inhibition of Ob-R signaling can be effectively achieved in a leptin-responsive cell in tissue culture. Ob-R signaling is conserved in a majority of mammalian species, and, as such, methods for inhibiting the same may be carried out in tissue culture cells derived from a majority of mammals. Examples of mammalian cell lineages in which Ob-R signaling is conserved include those derived from a human, mouse, or rabbit. Additionally, Ob-R signaling is conserved in cells derived from an array of tissue types, and as such, methods of the present invention may be carried out in cells derived from the same. Non-limiting examples of cell types include endometrial, follicular, adipose, placental, oocyte, preimplantation embryo, and fetal cell types. Specific endometrial cell types in which Ob-R signaling is conserved include endometrial epithelial and endometrial stromal cells. The methods for inhibiting Ob-R signaling, as disclosed herein, may be practiced using any cell which expresses the leptin receptor. The leptin receptor may be endogenous or exogenous to the cell. In vitro, the methods disclosed herein for inhibiting Ob-R signaling may be used to study the actions of leptin in a variety of cell types, or for the development of therapeutics for modifying Ob-R signaling. More specifically, the methods of the present invention may be used to study the roles of Ob-R signaling in reproduction, inflammation, proliferation, apoptosis, and angiogenesis. The methods of the present invention may be used to study and/or develop therapeutics for disease states relating to leptin misregulation, including but not limited to diabetes mellitus, acquired immune disease, cancer (including endometrial cancer), endocrine disorders of the adrenal cortex and pituitary glands, preeclampsia, endometriosis, polycystic ovarian syndrome, fertility, and obesity. The methods disclosed herein are not intended to be limited only for use with cells in culture.

Methods disclosed herein for inhibiting Ob-R signaling in a leptin-responsive cell may also be carried out in vivo. Inhibition of Ob-R signaling can be effectively achieved in cells within an organism. Inhibition of Ob-R signaling in cells within an organism may be achieved wherein the animal is human or non-human. Ob-R signaling is conserved in a majority of mammals, and, as such, methods for inhibiting the same may be carried out in a variety of mammals. Examples of mammals in which Ob-R signaling is conserved include humans, mice, and rabbits. The methods disclosed herein are not intended to be limited only for use with cells in any particular tissue or animal. In vivo, the methods disclosed herein for inhibiting Ob-R signaling may be used to alter leptin-dependent functions and/or leptin/Ob-R misregulation.

In one aspect, the present invention relates to methods for inhibiting Ob-R signaling in a leptin-responsive cell, the method comprising administering to a mammal a therapeutically effective amount of a peptide comprising a leptin sequence. In methods of the present invention, the peptide binds to, but does not activate, Ob-R signaling in a leptin-responsive cell of the mammal to which the peptide has been administered. The peptide effectively binds to Ob-R without transmitting the cellular signals that characterize the binding of leptin to Ob-R, thereby inhibiting Ob-R signaling in the treated mammal, the inhibition being relative to a matched mammal to which the peptide has not been administered, and also to a matched animal to which a scrambled version of the peptide has been administered.

The mammal to which the peptide is administered in the present invention may be any mammal which has genes that encode leptin and leptin receptor molecules or equivalents. An equivalent may be any protein bearing structural homology to a known leptin molecule, which is postulated to bind a protein bearing structural homology to a known leptin receptor molecule. The specific peptides disclosed may be administered to any mammal with a conserved leptin sequence. Examples of mammals with known conserved leptin sequences include humans, mice, and rabbits.

It is a further object of the present invention to provide methods for controlling leptin-dependent functions. In a preferred embodiment, administration of a peptide comprising a leptin sequence prevents embryo implantation in a mammal to which the peptide has been administered. Prior to the present invention, a direct correlate between blockade of the leptin receptor and prevention of embryo implantation was not known. A peptide comprising a leptin sequence may further be used to inhibit leptin actions in treating conditions characterized by abnormalities of leptin metabolism. Non-limiting examples of such conditions include endometriosis, diabetes mellitus, acquired immune disease, cancer, endocrine disorders of the adrenal cortex and pituitary glands, preeclampsia, endometriosis, polycystic ovarian syndrome and reduced fertility.

It is an object of the present invention to administer a peptide comprising a leptin sequence in a physiologically acceptable carrier in a therapeutically effective amount. A therapeutically effective amount is defined as any amount which is sufficient for inhibiting Ob-R signaling in a desired cell. A peptide of the present invention may be administered alone or in a combination with other pharmaceutical therapies. Pharmaceutical compositions of the present invention may comprise one or more of the peptides of the present invention. Administration of said peptide or peptides to a mammal may be either local or systemic and may be for short or long durations. A peptide or peptides of the present invention may be delivered to a mammal intramuscularly, or alternatively, by intravenous, subcutaneous, or oral administration. Within embodiments of the invention, the compositions described herein may be administered as part of a sustained release implant.

Because the therapeutic target of the present invention is extracellular, delivery of a peptide of the present invention need only be to the extracellular surface of a leptin-responsive cell. It is not a requirement of the present invention that a peptide comprising a leptin sequence be delivered intracellularly. In the methods of the present invention, the pharmaceutical challenge of targeted intracellular delivery, therefore, is overcome. In the present invention, a peptide comprising a leptin sequence is delivered to the extracellular surface of a leptin-responsive cell in which inhibition of Ob-R signaling is desired.

Prior to the present invention, the only demonstrated method for inhibiting Ob-R signaling in a cell comprised contacting a leptin-responsive cell with an effective amount of a functional antibody to Ob-R, the antibody characterized by its ability to prevent leptin binding to Ob-R. Blockade of Ob-R with a polyclonal antibody against the extracellular domain is known to inhibit the rate of formation of expanded mouse blastocyst and hatched blastocyst in an in vitro model of embryo development. In the Exemplification section that follows, blockade of Ob-R with an anti-Ob-R antibody was determined to inhibit the up-regulatory effects of leptin in endometrial cell culture. However, relatively high doses of antibodies were required to block Ob-R, which could potentially generate undesired immunological side effects in vivo. In contrast, in the methods of the present invention relatively low doses (3-300 nM) of a peptide comprising a leptin sequence were determined as sufficient for blocking Ob-R function in vitro and for preventing mouse embryo implantation in vivo. The methods of the present invention therefore have a distinct therapeutic advantage over antibody-based methods.

It is a further object of the present invention to provide methods for inhibiting Ob-R signaling in a leptin-responsive cell wherein the inhibition of Ob-R signaling in the cell results in an inhibition of the up-regulatory effects of leptin on a signaling event downstream of Ob-R. Leptin binding to its receptor promotes JAK-2 activation and triggers the phosphorylation of signal transducer and activator of transcription 3 (Stat3), that, in turn, activates a number of downstream signaling pathways. As exemplified, blockade of Ob-R by a peptide comprising a leptin sequence inhibits activation of a number of downstream events in both human and rabbit cells. More specifically, a peptide comprising a leptin sequence was shown to inhibit p-Stat-3, β3-integrin, IL-1 and LIF signaling. It is an object of the present invention that a peptide be used to inhibit any of the signaling events that arise from leptin binding to Ob-R. The signaling event may include regulation of gene expression, phosphorylation, and/or secretion of a direct or indirect target of Ob-R. It is a requirement that the signaling event inhibited be leptin-sensitive and downstream of Ob-R. Non-limiting examples of leptin-sensitive targets of ObR inhibited by the methods of the present invention include p-Stat-3, β3-integrin, IL-1R tI, LIF-R, LIF, IL-1β, and IL-1Ra.

It is a further object of the present invention to provide a method for identifying a peptide antagonist of Ob-R. The method comprises first providing a leptin or leptin equivalent sequence from a mammalian species. A leptin equivalent sequence may be any sequence which bears structural homology to a known leptin molecule, which is postulated to bind a protein bearing structural homology to a known leptin receptor molecule. A structural model of the provided leptin or leptin equivalent sequence bound to its receptor is then built. This may be accomplished by superimposing the three-dimensional structure of the leptin sequence on the three-dimensional structure of the G-CSF/G-CSF R complex. The structure of the leptin receptor complex is determined using any of a number of molecular modeling software programs available in the art. By comparing the residues of the G-CSF ligand that interact with G-CSF R, a determination of the region(s) of the leptin or leptin equivalent sequence which interact with its receptor can be made. A ligand/receptor complex other than G-CSF/G-CSF R may be utilized in identifying a peptide antagonist of Ob-R, as long as the complex bears presumptive structural homology to a leptin/Ob-R complex. Alternatively, identification of a peptide antagonist of Ob-R may be determined by a direct analysis of interacting residues of a leptin bound to Ob-R if the three-dimensional structure of such a complex is known. A peptide bearing the identified region of the leptin or leptin equivalent sequence is then synthesized and tested for its ability to inhibit ObR signaling in a cell. In a preferred embodiment, the peptide is tested in cell culture for its ability to bind to Ob-R and inhibit the up-regulatory effects of leptin on Ob-R signaling in a leptin responsive cell. It is a requirement that the identified peptide possess a high binding affinity for Ob-R and be an effective antagonist of Ob-R. In a preferred embodiment, an identified leptin region comprises any of residues 3-34 (LPA-1; SEQ ID NO:1) of the leptin sequence (helix I) or any of residues 70-95 (LPA-2; SEQ ID NO:2) of the leptin sequence (helix III). This method may include introducing conservative amino acid substitutions, deletions, and/or additions into the identified region, as long as the substitutions, deletions, and/or additions do not substantially prevent the binding of the peptide to ObR and do not negatively affect the antagonistic properties of the peptide. There are no strict requirements regarding the length of a peptide identified by this method.

Peptide compositions for use in the methods of the present invention are also herein provided. A composition of the present invention is characterized by its ability to inhibit the up-regulatory effects of leptin on ObR signaling in a leptin responsive cell. In a preferred embodiment, the composition comprises a peptide comprising a leptin sequence. The leptin sequence confers upon the peptide the ability to bind Ob-R with a relatively high affinity and specificity and be an effective antagonist of ObR. In one embodiment, the peptide comprises residues 3-34 (LPA-1; SEQ ID NO:1) of the leptin sequence (helix I) or a non-identical equivalent. In another embodiment, the peptide comprises residues 70-95 (LPA-2; SEQ ID NO:2) of the leptin sequence (helix III) or a non-identical equivalent. A non-identical equivalent is a peptide comprising a sequence substantially similar to either SEQ ID NO:1 or SEQ ID NO:2, wherein the non-identical equivalent retains the functional properties of SEQ ID NO:1 or SEQ ID NO:2. Functional properties include an ability to 1) compete with leptin for binding to Ob-R on a leptin-responsive cell and 2) block the leptin-dependent signaling in the leptin-responsive cell. A non-identical equivalent composition of the present invention may include the introduction of conservative amino acid substitutions, deletions, and/or additions into the peptide comprising a leptin sequence, as long as the substitutions, deletions, and/or additions do not substantially prevent the binding of the peptide to ObR and do not negatively affect the antagonistic properties of the peptide. There are no strict requirements regarding the length of a peptide composition comprising a leptin sequence for use in the methods of the present invention.

EXEMPLIFICATION

Example 1

Leptin Induce Increase in Leukemia Inhibitory Factor and its Receptor by Human Endometrium is Partially Mediated by Interleukin 1 Receptor Signaling Results:

More often than not many differences that are observed in response to cytokine treatments are related to different cell types. To provide a broader perspective primary human endometrial epithelial and stromal cells (EEC and ESC) and epithelial cell lines (HES and Ishikawa) were utilized to demonstrate treatment effects. To simplify the presentation of results and reduce redundancy, data provided herein supports the most dramatic results. Information is provided when plausible on treatment effects on the other cell types.

Leptin-Induced Effects on p-STAT3, LIF-R and LIF Levels in Human Endometrial Cell Cultures.

Figure 1:
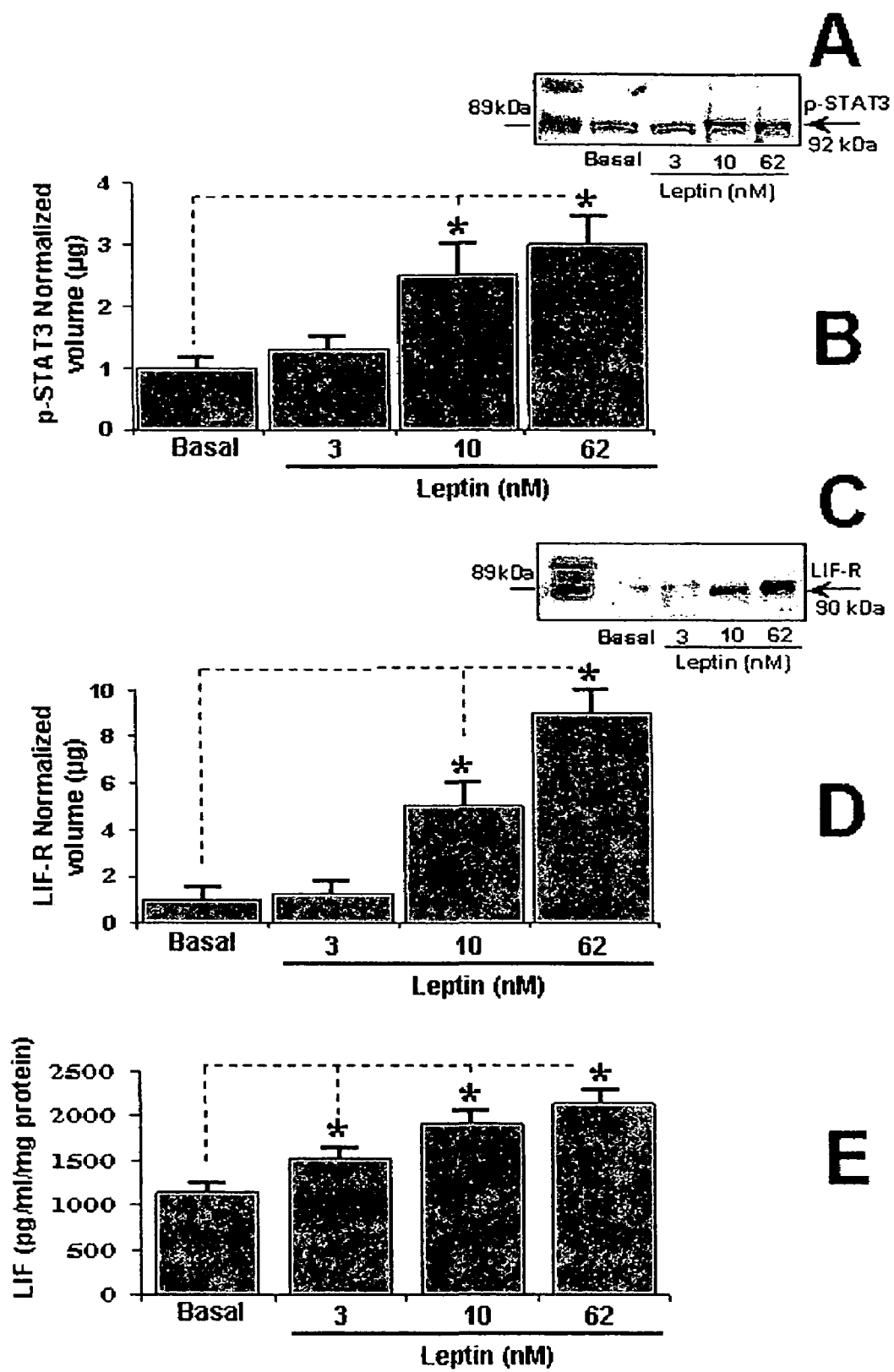
FIG. 1 shows leptin induced changes in the levels of phosphorylated STAT3, LIF-R and LIF by human endometrial cells. (A) Representative Western blot of p-STAT3 obtained from nuclear extracts of human endometrial epithelial cells (h-EEC) after 5 min of stimulation with leptin at increasing concentrations. (B) Quantitative analysis of p-STAT3 levels in h-EEC via Western blot following a 5 min of treatment with leptin. (C) Qualitative changes in LIF-R levels found in cellular extracts following a 24 hour treatment of h-EEC. The lysates were immunoprecipitated with anti LIF-R specific antibodies and the changes were visualized by Western blot as described in methods section. (D) Quantification of leptin-induced changes in LIF-R levels following densitometric analysis. (E) LIF levels in h-EEC in response to treatment with or without leptin for 24 h. All data was derived from a minimum of three independent experiments using different cell preparations. The results are presented in the graphs are the mean and SE. * denotes a "P" value of equal to or less than 0.05 when comparing levels in response to treatments to that of the non-treated controls.

After confirming via Western that the primary EEC and ESC and endometrial cell lines utilized herein had OB-R, leptin-induced effects on the levels of phosphorylated STAT3 was evaluated. A leptin-induced increase in the levels of p-STAT3 was observed in EEC (FIG. 1A). However, the increase was dose-dependent (FIG. 1B). For example, the leptin-induced increase of p-STAT3 levels in EEC was only found following treatment with the higher concentrations of leptin (10 and 62 nM; FIG. 1B). Similar effects were observed in the ESC and the Ishikawa and HES cell lines, however the response was not so dramatic (data not shown).

An increase in the levels of LIF-R after treatment of primary endometrial cells and endometrial cell lines with leptin was found by Western blot analysis. An increase in LIF-R levels was found after incubation of EEC with leptin at 10 and 62 nM doses (FIGS. 1C and D). Leptin (3-62 nM) induced a more moderate expression of LIF-R in HES (1.3-2 fold) than in Ishikawa cells (1.5-3 fold) or primary EEC (1.7-8 fold) and ESC (1.4-3.2 fold).

Treatment with leptin resulted in an increased level of LIF in primary EEC. The increase in LIF levels was dose-dependent (FIG. 1E). Similar patterns, although not so dramatic, were evident in leptin treatment of ESC and Ishikawa cells. No response was observed in the HES cells (data not shown).

Inhibition of Leptin-Induced Effects by OB-R Antagonists

Figure 2:
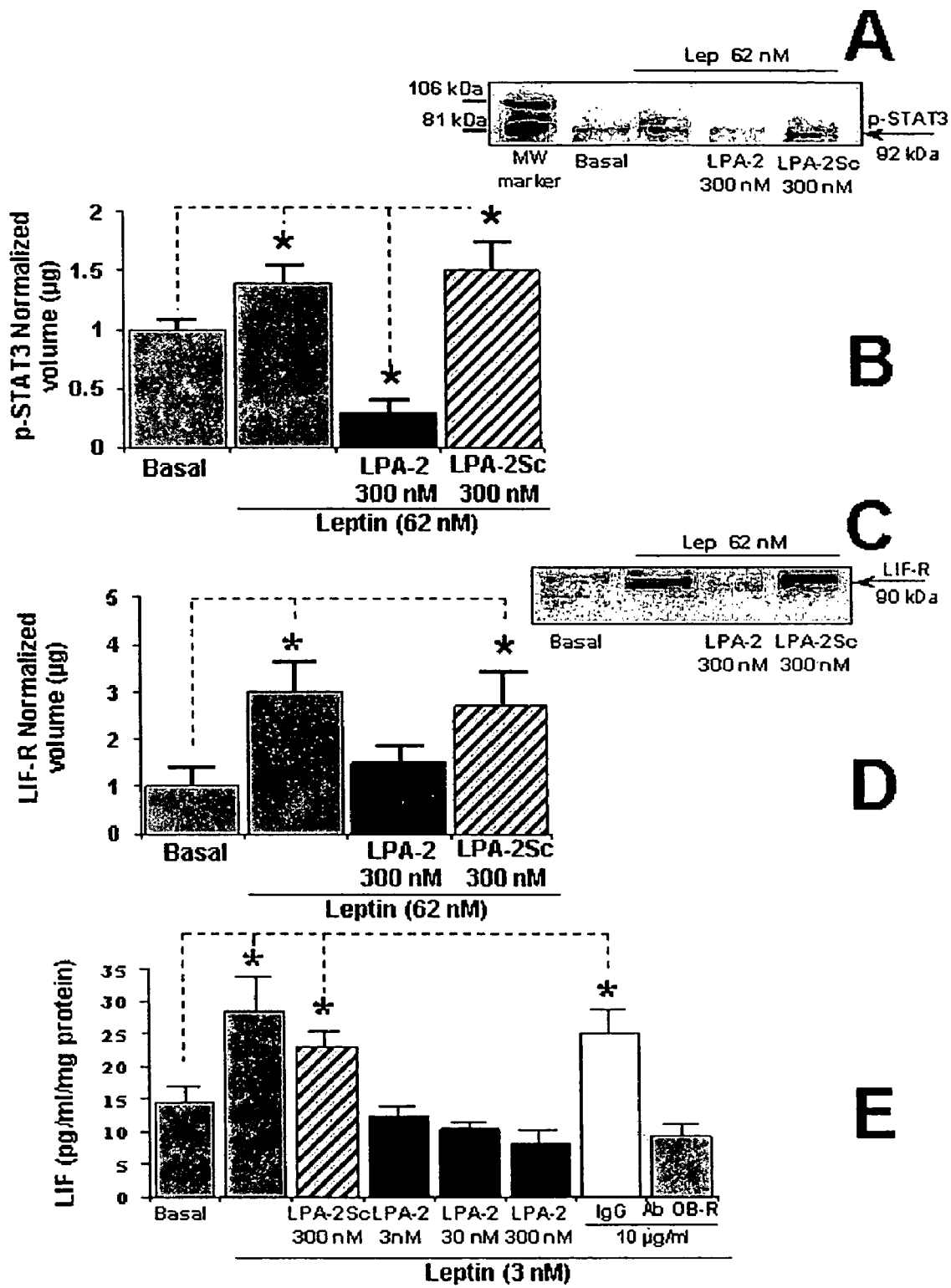
FIG. 2 illustrates leptin induced changes in the levels of phosphorylated STAT3, LIF-R and LIF are blocked by OB-R inhibitors. (A) Qualitative representation of a Western blot evaluating levels of p-STAT3 in Ishikawa cells after treatment with leptin and/or leptin and LPA-2. (B) Quantitative analysis of p-STAT3 levels. (C) Representative Western blot depicting changes in LIF-R levels found in Ishikawa cells after leptin and/or leptin and LPA-2 treatments. (D) Quantitative analysis of LIF-R levels. (E) LIF levels found in medium of cultured Ishikawa cells after treatments with leptin in the presence or absence of OB-R antagonists/inhibitors. The Ishikawa cells were cultured for 5 min to 24 h in medium containing leptin, leptin plus or anti OB-R antibodies. Controls included Ishikawa cells cultured with leptin plus LPA-2Sc or non-specific species-matched IgG. The levels of phosphorylated STAT3 (5 min) and LIF-R (24 h) was determined by Western blot analysis of the nuclear extracts and cellular immunoprecipitates, respectively. The amount of LIF in the medium was determined by ELISA (R&D System) and quantitative analyses of Western blot results were performed with the program TotalLab (version 2003.02, NonLinear Dynamics Ltd). The data was calculated from results of three or more experiments (n≥3) using different cell preparations. The results are presented in the graphs are the mean and SE. * denotes a "P" value of equal to or less than 0.05 when comparing levels in response to treatments to that of the non-treated controls.

Western blot analysis revealed that treatment of Ishikawa cells with leptin at a 62 nM concentration increased the levels of p-STAT3 over the non-treated controls. The antagonist, LPA-2 (300 nM) inhibited the leptin-induced increase, whereas LPA-2Sc had no effect (FIGS. 2A and B). Interestingly, LPA-2 treatment resulted in a decrease level of p-STAT3 when compared to the levels observed in the non-treated control Ishikawa cells (FIG. 2B). In a similar pattern, the levels of LIF-R were elevated over control following treatment with leptin (62 nM). Co-treatment with LPA-2 (300 nM) reduced the leptin-induced increase. As before, treatment with LPA-2sc had no effect on LIF-R levels (FIGS. 2C and D) when added in combination with leptin.

FIG. 2E illustrates a quantitative assessment of various inhibitors on leptin-induced effects on LIF levels found in the medium of cultured Ishikawa cells. Treatment with leptin (3 nM) increased the levels of LIF in the conditioned medium of cultured Ishikawa cells. The levels of LIF found in the conditioned medium following treatment with leptin in the presence of the scrambled peptide or IgG were not different than those from treatment with leptin alone. However, treatment of Ishikawa cells with both leptin and inhibitors of OB-R (either antibody or LPA-2) resulted in reduced LIF levels. Similar results were found in primary EEC. The inhibition of leptin-induced effects on LIF levels by OB-R antibody or LPA-2 in ESC was not as dramatic as that which was observed in the Ishikawa. Even though no leptin response was observed in the HES cells, the inhibitors were tested. As expected no effect was evident (data not shown).

Figure 3:
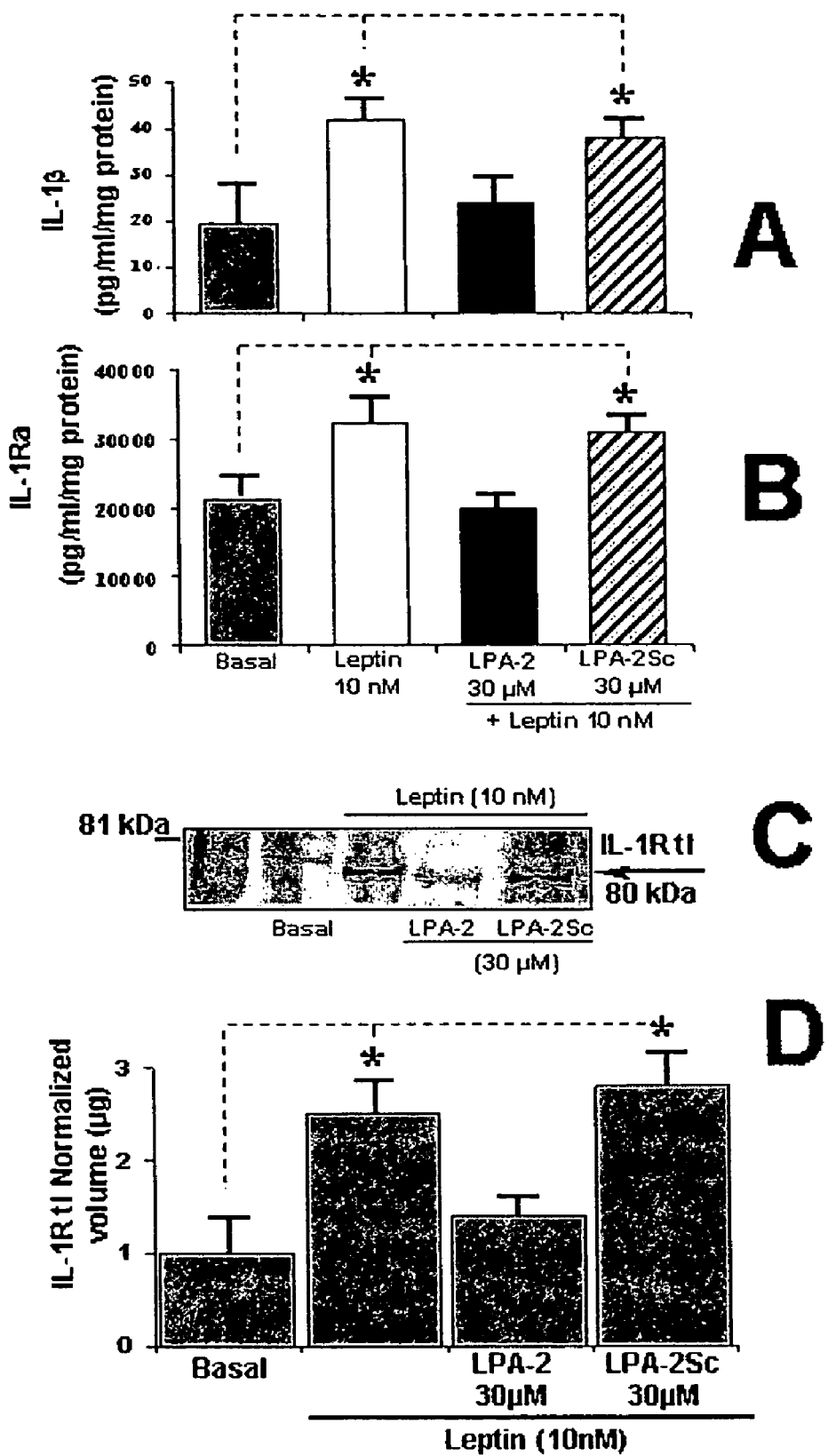
FIG. 3 shows leptin-mediated increase of IL-1β and IL-1Ra and IL-1R tI levels by human endometrial cells are blocked by OB-R inhibitors. Leptin (10 nM) increased the levels of IL-1β (A) and IL-1Ra (B) found in the conditioned medium of human endometrial epithelial cells (EEC). Leptin also augmented the levels of IL-1R tI (C) in EEC cultures. (D) Quantitative analysis of IL-1R tI levels. Interestingly, LPA-2 (30 μM) inhibited the leptin-induced changes in IL-1β (A) and IL-1Ra (B) levels. The cells were cultured for 24 h in a medium containing and LPA-2. Controls included EEC cultured with leptin plus LPA-2Sc. IL-1β and IL-1Ra concentrations in conditioned media were determined by ELISA (R&D System). IL-1R tI levels in immunoprecipitates of EEC extracts were determined by Western blot. Quantitative analyses of Western blot results were performed with the program TotalLab (version 2003.02, NonLinear Dynamics Ltd). All determinations were made in duplicate and the experiments were repeated at least three times. The results are presented in the graphs are the mean and SE. * denotes a "P"

Treatment of EEC with leptin resulted in elevated levels of IL-1β and IL-1Ra (FIGS. 3A and B). The leptin induced increase in IL-1 and IL-1Ra levels was abrogated by co treatment with LPA-2 and not affected by LPA2sc (FIG. 3B). Leptin also increase the levels of IL-1R tI and again LPA-2 inhibited the leptin-induced effects (FIGS. 3C and D). An analogous effect was observed in ESC and Ishikawa cells.

The leptin-induced effect on IL-1β and IL-1 levels was inconsistent in the HES cells (data not shown).

The Blockade of IL-1R tI Inhibits Leptin-Induced Effects on LIF-R Levels.

Treatment with IL-1β increased the levels of LIF-R found in Ishikawa cells in a dose dependent (3 and 10 nM) manner (FIGS. 4A and B). Moreover, when Ishikawa cells were treated with a combination of IL-1β and leptin (10 nM) a further increase of LIF-R levels was observed in comparison to the cells treated with IL-1β (10 nM) alone (see FIG. 4B). The leptin-induced increase of LIF-R levels in Ishikawa cells was abrogated by antagonists/inhibitors of IL-1R tI. The leptin-induced increase in LIF-R levels was partially blocked by the addition of IL-1Ra (1000 pg/ml) or anti IL-1R tI antibody (20 μg/ml). No effects were found when the antibody was substituted by non-specific species-matched IgGs (see FIGS. 4C and 4D).

Materials and Methods:

Reagents and Antibodies

Goat polyclonal anti-human LIF-Rq anti OB-R (anti-NH$_2$ terminal end of human OB-R) and monoclonal anti-IL-1R type I (IL-1R tI) antibodies, human recombinant leptin, IL-1β and IL-1Ra were obtained from R&D Systems Inc., MN. Antibodies for STAT3 (F-2) and phosphorylated STAT3 (p-STAT3, B-7) and non-specific mouse and goat IgGs were obtained from Santa Cruz Biotechnology, Inc., Santa Cruz, Calif. Anti-vimentin, anti-cytokeratin and anti-CD45 antibodies were from Dako Corporation, Carpinteria, Calif. Human recombinant insulin was obtained from Sigma Chemical Co., St Louis, Mo. Fetal bovine serum (FBS) was obtained from Gemini Bioproducts, Woodland, Calif., and Dulbecco's modified Eagle's medium (DMEM/F-12) and antibiotic-antimycotic mixture were from GIBCO BRL Products, Gaithersburg, Md. Other chemicals were obtained from Sigma Chemical Co., St Louis, Mo.

Endometrial Tissues

Endometrial tissues were obtained from hysterectomies of non-malignant etiologies under an IRB at the Vincent Center for Reproductive Biology (BRR-Massachusetts General Hospital, Boston, Mass.). Tissues were digested with proteases for endometrial cell isolation as described elsewhere (Gonzalez et al., *Hum. Reprod.* 14: 2485-2492 (1999)). Briefly, endometrial biopsies were minced and treated with collagenase I (0.1%)-DNAse 1 (0.005%) for 1 h at 37° C. After gland sedimentation endometrial stromal cells (ESC) were separated from supernatants. EEC were purified of ESC and macrophage contaminants by repeated incubation at 37° C. in a Falcon flask. Stromal and epithelial cell dispersions were counted in a haemocytometer and cell viability (≧90%) was assessed by optical microscopy using the Trypan Blue exclusion method. To assess homogeneity of cell preparations several specific monoclonal antibodies were used in cell smears (Gonzalez et al., *Hum. Reprod.* 14: 2485-2492 (1999)), i.e., anti-vimentin (ESC+), cytokeratin (EEC+) and CD45 (leukocyte+). Homogeneity of cell preparations was higher than 98%.

Cell Cultures and Treatments.

Primary human endometrial cells (ESC and EEC) were cultured for 5-9 days in DMEM-F12 medium containing 5% fetal bovine serum (FBS), 5 μg/ml insulin, 1% amphoptheri-cin B, 100 μg/ml streptomycin and 100 U/ml penicillin until they were 80% confluent. Two types of endometrial epithelial cell lines, HES (originally derived from a benign proliferative endometrium) and Ishikawa (human endometrial epithelial adenocarcinoma, ECACC 9832301, Wiltshire, England) were cultured under the same conditions described above. The cells were washed twice with 100 mM phosphate saline buffer (PBS), pH 7.2 and cultured for additional 2 days in the same medium but without FBS (basal medium). Cells were washed as described before and cultured in basal medium containing leptin (0, 3, 10 or 62 nM) or IL-1β (0.6, 3 and 10 nM).

The anti-OB-R antibody (10 and 20 μg/ml) and LPA-2, a specific inhibitor of OB-R (3, 120, 300 nM or 30 μM) were used to assess whether leptin-induced effects were regulated primarily by the OB-R. Non-specific species-matched IgGs to the OB-R antibody and a scrambled version of LPA-2 (LPA-2Sc) served as negative controls (Gonzalez and Leavis, *Endocrine* 21: 185-195 (2003)). Inhibitors of IL-1R were used (monoclonal antibody anti-IL-1R tI and IL-1Ra) to assess whether leptin activated IL-1 induced signaling pathways or just activated similar components responsible for LIF/LIF-R expression. Treatment with the cytokine, inhibitor or the two combined was implemented for 5, 15, 30 and 60 min, and 24 and 48 h. The cells were prepared for Western blot analysis. The conditioned media was collected, lyophilized and stored at −80° C. until analysis for LIF, IL-1β and IL-1Ra by ELISA could be performed. Duplicate wells were run for each treatment and the experiments repeated at least three times with different cell preparations.

Cell Lysates

Endometrial cells were washed with ice-cold PBS and lysed by homogenization on ice with lysis buffer A [20 nM Tris, pH 7.4, containing 137 nM NaCl, 2 mM EDTA, 10% glycerol, 50 mM β-glycerophosphate, 1% Nonidet P-40 and a mixture of proteases and phosphatase inhibitors composed of 100 μM antipain, 0.1 mg/ml trypsin inhibitor, protease inhibitor cocktail 1:50 (Sigma), 50 nM NaF, 2 mM phenyl-methylsulfonyl fluoride, and 2 mM sodium orthovanadate]. Cellular lysates were centrifuged at 2400 g at 4° C. for 10 min. For nuclear lysates the cells were scraped from the culture plates and homogenized with lysis buffer B (10 nM Tris, pH 7.4, 0.25 M sucrose, 0.1 mM EDTA containing the same mixture of protease and phosphatase inhibitors as buffer A). Protein concentrations were determined using the Bradford protein assay (BioRad Laboratories Inc., Hercules, Calif.).

Immunoprecipitation.

30 μg of protein from nuclear or cellular lysates were incubated in ependorf tubes containing 0.5 μg of primary antibodies (anti-LIF-R, OB-R, STAT3 and p-STAT3 diluted in buffer A) for 2 h at 4° C. under constant stirring. The immuno-complexes were incubated with 20 μl of Protein G-Agarose (Amersham Pharmacia Biotech) diluted 1:1 with buffer A for a 2 additional hours under constant stirring. The beads were centrifuged for 1 min at 1000 g and washed with buffer A containing 0.5 M NaCl followed by a final wash with buffer A.

Western Blot

Cellular lysates and their immunoprecipitates containing 10-30 μg of protein plus Laemmli buffer (1:1) were incubated at 95° C. for 5 min. Electrophoresis was performed at 220 V for 5 min followed by 130 V for 45 min (BioRad, electrophoresis apparatus) on 7.5% (for STAT3, p-STAT3, LIF-R and IL-1R tI) and 10% (for OB-R) SDS-PAGE gels. Nuclear lysates were also used to detect p-STAT3. Electroblotting onto 0.2 μm nitrocellulose membranes was performed at 22 V overnight at 4° C. in 48 nM Tris-39 nM glycine buffer containing 0.037% SDS and 20% methanol. Membranes were washed with 20 mM Tris, 137 mM NaCl pH 7.4 buffer containing 0.5% Tween 20 (v/v) (wash buffer) and incubated for 1 h at room temperature in blocking buffer containing low fat dried milk (5%, w/v) in wash buffer. The membranes were subsequently incubated at room temperature for 1 h with 2 µg/ml of anti OB-R, LIF-R and 1 µg/ml of IL-1R tI, STAT3 and p-STAT3 antibodies in blocking buffer. After washing, the membranes were incubated for 30 min in wash buffer containing 2.5% normal horse or rabbit serum (Vector Laboratories). Immune-complexes were detected with biotinylated horse anti-mouse or rabbit anti-goat antibodies (Vector Laboratories) followed by incubation with streptavidin-horseradish peroxidase-conjugate (Amersham) for 30 min at room temperature. Specific bands in the blots were visualized using an ECL-chemiluminescent assay (Amersham) and Imagetek-B film (American X-ray & Medical Supply, Rancho Cordoba, Calif.). Non-specific mouse and goat IgGs (Santa Cruz Biotechnology) were used instead of primary antibodies to produce negative control blots.

To quantitatively assess the effects of cytokines and inhibitors of OB-R and IL-1R tI on the antigen expression, the blots were scanned and analyzed (TotalLab version 2003.02, Non-Linear Dynamics Ltd).

Determination of LIF, IL-1β and IL-1Ra Secretion by Human Endometrial Cells

Conditioned media from cells cultured under the experimental conditions described above were used to quantify the secretion of LIF, IL-1β and IL-1Ra by ELISA (Quantikine$^R$, R&D Systems). The experiments were replicated three times and standards, controls, and samples were assayed in duplicate. Cytokine concentrations as determined by ELISA were within the range of the standard curve and were expressed in pg/ml/mg protein. The intra- and interassay coefficients of variation were between 5-8% and 8.5-10%, respectively. The lowest detectable concentration of each cytokine by ELISA was LIF (9 pg/ml), IL-1 (0.11 pg/ml) and IL-1Ra (15.6 pg/ml). These concentrations are similar to those reported by the manufacturer. LIF-ELISA is reported by the manufacturer to have a sensitivity of less than 8 pg/ml for both natural and recombinant human LIF and 100% specificity (no significant cross-reactivity or interference with a diversity of human and mouse cytokines and growth factors was observed). The performance characteristics for human IL-1β and IL-1Ra ELISAs reported are: 100% specificity, sensitivity 0.1 pg/ml and 14 pg/ml, respectively.

Statistical Analysis

A one-way ANOVA test with Dunnett error protection and a confidence interval of 95% was used from the Analyse-it for Microsoft Excel (Leeds, UK, htpp://www.analyse-it.com) for data analysis. Data are expressed as mean±SEM. Values for $p<0.05$ were considered statistically significant.

Example 2

A Peptide Derived from the Human Leptin Molecule is a Potent Inhibitor of the Leptin Receptor Function in Rabbit Endometrial Cells Design, Synthesis, Purification and Characterization of LPA-2

LPA-2 and LPA-2Sc were synthesized using solid-phase peptide synthesis. After HPLC purification the peptides were ≧98% pure. Determination of molecular weight of LPA-2 peptides by mass spectral analysis demonstrated a unique peak corresponding to the calculated MW of 2982 Da for both LPA-2 and LPA-2Sc.

Results from circular dichroism spectroscopy measurements used to predict LPA-2 structure showed that this peptide conserves the alpha-helical structure found in the native human leptin molecule (Gonzalez et al., Mol. Hum. Reprod. 9: 151-158 (2003)). Analysis of the secondary structures and hydrophobicity/hydrophilicity profiles of LPA-2 and its scrambled version using the program Protean (DNASTAR) indicated that the two peptides have a significantly different secondary structure. Therefore, LPA-2Sc is a reliable negative control for testing LPA-2 binding to OB-R and its specific effects on rEC cultures.

Expression of Functional OB-R by Rabbit Endometrial Cells and Binding of LPA-2 to OB-R After the purification steps, homogenous preparations of rabbit endometrial stromal (rESC) and epithelial cells (rEEC) were successfully obtained. Immunocytochemical studies showed that rESC expressed vimentin (FIG. 6Aa), but not cytokeratin. In contrast, rEEC did not express vimentin but were positive for the epithelial cell marker, cytokeratin (FIG. 6Ac).

Interestingly, both cellular types constitutively expressed OB-R (FIGS. 6Ab and Ad). Addition of leptin, LPA-2 or anti-OB-R antibody to cultures of rESC or rEEC did not affect the expression of OB-R. Negative controls using cells incubated with non-specific species-matched IgGs showed no staining for any of the antigens tested (FIG. 6e).

Western blot analysis of lysates from cell cultures corroborated the immunocytochemical findings. A main band of approximately 190 kDa corresponding to the full length of OB-R was found in all protein lysates from rESC and rEEC cultured in basal medium or medium containing the tested compounds (FIG. 6B). Results from competitive binding studies between human leptin and LPA-2 show that $^{125}$I-leptin bound to OB-R from cellular lysates was displaced by addition of LPA-2 (FIG. 6C). LPA-2 (Ki~$0.6\times10^{-10}$ M) but not LPA-2Sc specifically binds to OB-R expressed by rabbit endometrial cells (rEEC and rESC).

Up-Regulation of p-Stat3 Expression by Leptin in Rabbit Endometrial Cells and Inhibition by Anti-OB-R Antibody and LPA-2.

To test the functionality of OB-R expressed by the rabbit endometrial cells, p-Stat3 phosphorylation was investigated following leptin treatment. FIG. 7 shows the immunocytochemical results obtained with rESC. The basal expression of p-Stat3 (FIG. 7A) was up-regulated by leptin (FIG. 7B). Similar results were obtained for rEEC (not shown).

LPA-2 significantly inhibits the leptin up-regulation of Stat3 phosphorylation (FIG. 7D) to a degree similar to that found with anti-OB-R antibody treatments (data not shown). The LPA-2 blockade of p-Stat3 expression appears to be specific since this effect was found at very low concentrations of LPA-2 (doses ranged from 3 to 300 nM) and was not observed with LPA-2Sc (FIG. 7C) at the same concentrations. Negative controls using cells incubated with non-specific species matched IgGs showed no staining for any of the antigens tested (FIG. 7E).

Results from western blot determinations of p-Stat3 expression by rESC and rEEC confirmed the immunocytochemical findings. An 81 kDa band corresponding to p-Stat3 was found in samples from rESC (FIGS. 7F and G) and rEEC (FIGS. 7H and I). Both cell types exhibited increased p-Stat3 expression after incubation with leptin (3 nM).

The antibody specific for the NH2 terminal end of human OB-R (at all concentrations assayed) effectively blocks the receptor function in the cell cultures by decreasing the leptin up-regulation of Stat3 phosphorylation in rESC (FIG. 7F) and rEEC (FIG. 7H). This effect appears to be specific since the cells incubated with non-specific goat IgGs did not down-regulate p-Stat3 after leptin treatment (See last lane in FIGS. 7F and H).

As it was found in the immunocytochemical studies, LPA-2 (3 to 300 nM) effectively inhibited the basal expression of p-Stat3 in rESC (FIG. 7G) and rEEC (FIG. 7I). No inhibitory effect on p-Stat 3 expression was seen when the cells where incubated with LPA-2Sc (See last lane in FIGS. 7G and I).

Leptin Regulation of IL-1R tI Expression by Endometrial Rabbit Cells.

Results from immunocytochemical and western blot studies on leptin regulation of IL-1R tI expression and the antibody and LPA-2 effects were similar in rESC and rEEC. FIG. 8 shows results from rESC. Rabbit endometrial cells cultured in basal medium weakly express IL-1R tI (FIG. 8Aa). Leptin (3 nM) substantially up-regulates IL-1R tI expression (FIG. 8Ab). Moreover, as was found for p-Stat3 expression, the leptin effect on IL-R tI expression was completely abolished by the addition of LPA-2 (FIG. 8Ac). However, this LPA-2 inhibitory effect was more evident in rESC than in rEEC cultures (data not shown). Cells incubated with non-specific mouse IgGs did not show any positive staining for IL-1R tI (FIG. 8Ad).

The western blot analysis of IL-1R tI expression from the cellular lysates of rESC cultures (FIGS. 8B and C) confirmed the immunocytochemical results. The incubation of rESC cultures with anti-OB-R antibody was used as a positive control for the OB-R inhibition (FIG. 8B). The increase in intensity of the 80 kDa band corresponding to IL-1R tI in the blot from protein extracts of rESC following incubation of the cells with leptin (3 nM, number 2 in FIG. 8B) compared to cells cultured in basal medium (number 1 in FIG. 8B) demonstrates the leptin up-regulation of IL-1R tI expression. The addition of anti-OB-R antibody neutralized the leptin up-regulation of IL-1R tI (number 3 in FIG. 8B), further demonstrating the specificity of the leptin effect. Furthermore, incubation of rESC with non-specific goat IgGs and leptin did not prevent the leptin up-regulation of IL-1R tI expression (number 4 in FIG. 8B).

Interestingly, LPA-2 exhibited inhibitory effects on leptin up-regulation of IL-R tI expression in rESC cultures similar to those found with anti-OB-R antibody (FIG. 8C). LPA-2 (number 3 in FIG. 8C) inhibited the basal expression of IL-1R tI by rESC (number 2 in FIG. 8C). Moreover, leptin up-regulation of IL-1R tI (number 1 in FIG. 8C) was significantly decreased by LPA-2 in a dose-response manner (number 4 and 5 in FIG. 8C).

In contrast, LPA-2Sc did not alter the leptin effect on IL-1R tI expression (number 6 in FIG. 8C). Results from western blot of rEEC lysates were similar (data not shown).

Leptin Regulation of LIF Secretion and LIF-R Expression by Rabbit Endometrial Cells.

The effects of leptin on LIF-R expression in rESC and rEEC were also investigated. It was found that leptin up-regulates the expression of LIF-R in both cell types. The immunocytochemical results from LIF-R staining in rESC are shown in FIGS. 9A-D. The basal expression of LIF-R (FIG. 9A) was increased by leptin (FIG. 9B). Once again, the incubation of rESC cultures with leptin plus LPA-2 showed that this peptide also inhibited the leptin effect on LIF-R expression (FIG. 9C). Negative controls for LIF-R staining with rESC incubated with non-specific goat IgGs exhibited no staining (FIG. 9D).

Western blot analysis of rESC and rEEC lysates for LIF-R were also performed. FIG. 9E shows representative results from rEEC. Leptin at 3 nM significantly increases the expression of LIF-R (90 kDa band; number 2 in FIG. 9E) relative to the basal level (number 1 in FIG. 9E). The addition of anti OB-R antibody to rEEC cultures containing leptin (3 nM) completely inhibited LIF-R expression (number 3 in FIG. 9E) in contrast to the negative control, consisting of cells incubated with non-specific goat IgGs (number 4 in FIG. 9E). LPA-2 totally inhibited the leptin effect on LIF-R expression at 30 and 120 nM doses (number 5 and 6 in FIG. 9E, respectively). Incubation of rEEC with LPA-2Sc did not prevent the leptin up-regulation of LIF-R (number 7 in FIG. 9E).

LIF secretion by rabbit endometrial cell cultures was low but detectable by the ELISA kit. LIF concentrations were divided by the milligrams of total protein present in the cell lysates and expressed as pg/ml/mg protein.

Secretion of LIF by rEEC was higher than in the case of rESC (not shown) under all-experimental conditions. Moreover, leptin increased LIF secretion in a dose-dependent manner, the effect being more evident in rEEC. Moreover, the blockade of OB-R with the OB-R antibody abolished the leptin effect (FIG. 10A).

Interestingly, the addition of LPA-2 at doses from 3 to 300 nM significantly inhibited the leptin (3 nM) induction of LIF secretion by rEEC (FIG. 10B). A higher leptin dose (10 nM) resulted in a two-fold increase in LIF secretion by rEEC which was effectively inhibited by the addition of equimolar LPA-2 (FIG. 10C).

Materials and Methods

Hormones, Antibodies, and Reagents.

Human recombinant leptin, monoclonal antibodies anti IL-1R tI, anti LIF-R, and goat polyclonal antibody to the NH2 terminal end of human OB-R were provided by R & D System Inc., MN. Monoclonal antibody (B-7) for phosphorylated Stat3 (p-Stat3) and non-specific mouse and goat sera were obtained from Santa Cruz Biotechnology, Inc., Santa Cruz, Calif. Anti-vimentin, anti-cytokeratin (pan-cytokeratin) and anti-CD45 antibodies were from Dako Corporation, Carpinteria, Calif. $^{125}$I-human leptin was obtained from New England Nuclear (NEN, MA), and human recombinant insulin and MCDB-105 culture medium were obtained from Sigma Chemical Co., St Louis, Mo. Fetal bovine serum (FBS) was obtained from Gemini Bioproducts, Woodland, Calif., and Dulbecco's modified Eagle's medium (DMEM) and antibiotic-antimycotic mixture were provided by GIBCO BRL Products, Gaithersburg, Md. Other chemicals were from Sigma.

Design of LPA-2.

To design a potential leptin peptide antagonist (LPA), data from the following sources was analyzed: (a) Comparison of leptin sequences from different species using CLUSTAL W 1.81 (a multiple sequence alignment program). (b) Reported studies on the binding and biological activities of leptin analogs (deletion and mutants) (Gonzalez and Leavis, *Endocrine* 21: 185-195 (2003); Fedorcsak and Storeng, *Biol. Reprod.* Jun. 25 [Epub ahead of print] (2003); Kloek et al., *J. Biol. Chem.* 277: 41547-41555 (2002); Aghajanova et al., *Fertil. Steril.* 79: 808-814 (2003)). (c) Building of a model for the leptin-leptin receptor complex using program "O" (Nachtigall et al., *J. Clin. Endocrinol. Metab.* 81: 801-806 (1996)) based on a model previously proposed for leptin binding to OB-R (Gonzalez and Leavis, *Endocrine* 16: 21-28 (2001)). For this purpose, the four-helix bundle structure of leptin (Gonzalez et al., *Mol. Hum. Reprod.* 9: 151-158 (2003)) onto G-CSF in the complex with its receptor G-CSF R was superimposed. From the analysis of these data, LPA-2 to contain residues 70-95 of helix III of the human leptin molecule was designed.

Synthesis and Purification of LPAs

LPA-2 (26 amino acids residues; SRNVIQISNDLENL-RDLLHVLAFSKS; SEQ ID NO:2) and a scrambled version of this peptide (LPA-2Sc; VAEVLNRSDLIQRISF-SLDLNNSKLH; SEQ ID NO: 3) were synthesized by solid-phase peptide synthesis (Applied Biosystems, Model 431A Peptide Synthesizer) using 9-fluorenylmethoxycarbonyl (fmoc) chemistry. The peptides were purified using a C18 preparative high performance liquid chromatography (HPLC) column. The program Protean (DNASTAR.) was used to compare the LPA-2 and LPA-2Sc peptides to insure that the two peptides had dissimilar secondary structures.

Because LPA-2 peptides proved to be sparingly soluble in water, dimethyl-sulphoxide (DMSO) was used as solvent for the preparation of concentrated solutions of these peptides. After solubilization with DMSO it was then possible to dilute the peptides either in 50 mM Tris and 100 mM NaCl, pH 8.5 to promote proper re-folding or directly in culture medium to obtain the desired concentrations for the binding and cell culture experiments.

Protein Analytical Procedures

The purities of LPA-2 and LPA-2Sc were evaluated by reversed phase HPLC. Circular dichroism spectroscopy was used to assess LPA-2 and LPA-2Sc secondary structures. The molecular masses of the peptides were determined by mass spectral analysis on a Voyager-RP Biospectrometer MALDI-TOF Workstation (Perseptive Biosystems, Cambridge, Mass.). Spectra were averages of approximately 200 scans.

Endometrial Tissues

Uteri from non-mated female New Zealand white rabbits were kindly provided by Dr. M. Ortega, (Schepens & Eyes Institute, Harvard University, Boston, Mass.). The rabbit uteri used for preparation of endometrial cells were obtained under an approved IACUC protocol. Endometrial tissues were scraped from the uteri and then digested with proteases for isolation of endometrial cells as described elsewhere (Simon et al., *Endocrinology* 134: 521-528 (1994)). Briefly, endometrial tissues were minced and treated with collagenase I (0.1%)-DNAse I, 0.005% for 1 h at 37° C. rEEC were purified of rESC and macrophage contaminants by repeated incubation for 1-2 h at 37° C. in a Falcon flask. rEEC and rESC dispersions were counted in a haemocytometer and cell viability was assessed by optical microscopy using the Trypan Blue exclusion method. The mean of cell viability was higher than 95%. The homogeneity of cell preparations was assessed by the expression of cytokeratin (EEC+) vimentin (ESC+) and CD45 (leukocytes+) using specific antibodies (Simon et al., *Endocrinology* 134: 521-528 (1994)). Homogeneity of cell preparations was approximately 98%.

Cell Cultures

Rabbit endometrial cells ($5 \times 10^5$ cells/well) were cultured for 5-9 days in DMEM-MCDB105 (3:1) medium containing 10% fetal bovine serum (FBS), 5 µg/ml insulin, 1% amphoptericin B, 100 µg/ml streptomycin and 100 U/ml penicillin until confluent layers were obtained. The cells were washed twice with 100 mM phosphate saline buffer (PBS)-2% BSA (w/v), pH 7.2 and cultured for an additional 2 days in the same medium but without FBS (basal medium). This procedure was performed to reduce any effects of cytokines from FBS on the phosphorylation rate of Stat3 as well as the expression of other cytokines and their receptors. Cells were washed as described before and cultured in basal medium containing leptin (0-10 nM), OB-R antibody (1-20 µg/ml) and/or LPA-2 peptides (0-300 nM). Cultures were stopped at 24 h and the cells were used for immunocytochemistry, binding studies and western blot analysis. The conditioned media were collected, lyophilized and stored at 80° C. for ELISA determinations. Duplicate wells were run for each treatment and the experiments repeated at least three times with different cell preparations from different rabbits. Controls were the same cellular preparations cultured in basal medium containing non-specific goat IgGs and LPA-2Sc.

Determination of LIF Secretion by Rabbit Endometrial Cell Cultures

IL-1β from rabbits and humans have sequence differences, but no data is available concerning the sequence of rabbit LIF. In addition, there are no commercial kits for measuring rabbit IL-1β or LIF. However, because LIF has been suggested to be important for mammalian reproduction, to measure LIF in rabbit culture supernatants using a quantitative method designed for determining human LIF was attempted. Conditioned media (n=3 per treatment) from rESC and rEEC cultured in the experimental conditions described above were used to quantify the secretion of LIF by ELISA (LIF-Quantikine$^R$, R&D Systems). Standards, controls, and samples were assayed in duplicate. The intra- and interassay coefficients of variations were between 0.7-12% and 3-7%, respectively. According to the manufacturer, the performance characteristics of the ELISA were as follows: 100% specificity and sensitivity less than 8 pg/ml for both natural and recombinant human LIF; no significant cross-reactivity or interference was observed with a great diversity of human and mouse cytokines and growth factors.

Immunocytochemistry:

The rabbit endometrial cells were cultured as described above in duplicate on 8-well glass-bottom culture plates (Nalgene Nunc International, Naperville, Ill.) and fixed with methanol at −20° C. for 20 min for immunocytochemical studies. All the antibodies tested were diluted in PBS-2% BSA (w/v; buffer A).

The expression of OB-R was assessed by incubation of rEC for 1 h at room temperature with goat antibodies directed towards the amino terminal ends of human OB-R (R&D system) diluted 1:80 in buffer A.

Anti IL-1R tI (1 µg/ml), anti LIF-R (2 µg/ml), anti vimentin (1:50), anti cytokeratin (1:50) and anti p-Stat3 (1 µg/ml) antibodies were used to assess the expression of the respective antigens by rEEC and rESC cultures. After incubation with primary antibodies the cells were incubated with a streptavidin-biotin-alkaline phosphatase system according to the manufacturer directions (Vectastain, ABC-AP kit, Vector Laboratories, Burlingame, Calif.) and counter-stained with hematoxylin (Dako). Negative controls included cell preparations in which the primary antibodies were substituted by irrelevant species matched IgGs.

Preparation of Cell Lysates.

After culture in the presence of leptin, LPAs or antibodies, the endometrial cells were washed with ice-cold PBS and lysed by homogenization on ice with lysis buffer [20 nM Tris, pH 7.4, containing 137 nM NaCl, 2 mM EDTA, 10% glycerol, 50 mM β-glycerophosphate, 50 nM NaF, 1% Nonidet P-40, 2 mM phenyl-methylsulfonyl fluoride, 2 mM sodium orthovanadate, 100 µM antipain, 0.1 mg/ml trypsin inhibitor and protease cocktail inhibitor 1:50 (Sigma)]. Cellular lysates were centrifuged at 24000 g at 4° C. for 10 min. Protein concentrations were determined using the Bradford protein assay (BioRad Laboratories Inc., Hercules, Calif.).

Western Blot Analysis

Protein extracts from cell lysates were combined (1:1) with Laemmli buffer (2× concentrated) and 10 µg of proteins were loaded per lane on 7.5% (for p-Stat3, IL-1R tI and LIF-R) and 10% (for OB-R) SDS-PAGE gels. Electrophoresis was performed at 65 V for 1-1.5 h (BioRad, electrophoresis apparatus). Electroblotting onto 0.2 µm nitrocellulose membranes was performed at 22V overnight at 4° C. in 48 nM Tris-39 nM glycine buffer containing 0.037% SDS and 20% methanol. Membranes were blocked for 1 h at room temperature in 20 mM Tris, 137 mM NaCl pH 7.4 buffer containing 0.5% Tween 20 (v/v) (wash buffer) supplemented with 5% Amersham blocking reagent (blocking buffer) and rinsed three times with wash buffer. The membranes were subsequently incubated at room temperature for 1 h with 2 µg/ml of anti OB-R, IL-1R tI, LIF-R and p-Stat3 antibodies in blocking buffer. Detection was performed by incubation with biotinylated anti-mouse or anti-goat antibodies followed by incubation with streptavidin-horseradish peroxidase-conjugate (Amersham Pharmacia Biotech) for 30 min at room temperature. Positive specific antigen-antibody reactions in the blots were visualized using an ECL-chemiluminescent assay (Amersham) followed by exposure on KODAX X-Omat AR film (IBI-Kodak Ltd, Cambridge, U.K.). Non-specific mouse and goat IgGs (Santa Cruz Biotechnology) were used instead of primary antibodies to produce negative control blots.

Binding Assays $^{125}$I-human leptin served as ligand and LPA-2 and LPA-2Sc as competitors for the binding to OB-R in cellular extracts. All compounds were diluted in assay buffer (50 mM Tris and 100 mM NaCl, pH 8.5) to promote proper re-folding. Each assay tube contained 50 µl of cellular lysate (100 µg protein from $10^6$ cells cultured for two days in basal medium), 50 µl of $^{125}$I-human leptin (100.000 cpm), and 50 µl of LPAs (providing $10^{-5}$-$10^{-14}$ M/tube). The tubes were incubated for 24 h at room temperature. Then, 250 µl of 1% BSA (w/v) and 500 µl of 20% polyethylene glycol (w/v) in PBS were added and the tubes were incubated for an additional 12-h period at 4° C. The tubes were centrifuged at 12.000 g for 15 min at 4° C. After careful aspiration of supernatant and complete drying of the tube-walls with filter paper, $^{125}$I-human leptin binding in the precipitates was measured (Beckman 5000, counter). The binding of $^{125}$I-leptin to OB-R in absence of LPAs was set at 100%, and LPA competitive binding values were expressed as percentages of total cpm. Affinity binding constants for LPAs were calculated from the competition curves.

Statistical Analysis

A one-way ANOVA test with Dunnett error protection and a confidence interval of 95% was used from the Analyse-it for Microsoft Excel (Leeds, UK, htpp://www.analyse-it.com) for data analysis. Data are expressed as mean±SEM. Values for P<0.05 were considered statistically significant.

Example 3

Mous Embryo Implantation Requires Endometrial Leptin Signaling

Impact of OB-R Inhibitors on Mouse Embryo Implantation.

It was determined that the vehicle solution did not have any toxic effect on implantation in the treated mice. Analysis of implantation sites in mouse endometria after mating showed that a single injection of LPA-2 or LPA-1 (3 µM/10 µl) at Day 3 of pregnancy significantly impaired implantation. Only 20% of the uterine horns treated with LPA-2 or LPA-1 exhibited implantation sites (FIG. 11). In contrast, 77% of the horns injected with negative controls (LPA-2Sc or LPA-1Sc) showed implanted embryos (FIG. 11). Moreover, 81% of implanted embryos were found in the control horns versus 19% in LPA-2 treated horns.

Preliminary results from intra-uterine injection of anti OB-R specific antibodies (1.5 µg/horn) showed no reduction of implantation rate. However, higher doses of the blocking OB-R antibody (7.5 µg/horn) negatively affects mouse implantation in contrast to the control horns treated with non-specific goat IgGs.

The embryos that implanted in LPA-1, LPA-2 or anti OB-R antibodies treated horns were mainly found in the distal portion of the uterine horn—furthest from the OB-R inhibitor injection site. In contrast, the implanted embryos in LPA-1Sc or LPA-2Sc, vehicle or IgG treated mice were found uniformly distributed throughout the uterine horn.

The Effects of OB-R Inhibitors on the Development of Mouse Embryos In Vivo

Analysis of recovered embryos after intra-uterine injections of OB-R inhibitors showed that the development of unimplanted embryos was arrested in LPA-2 or anti OB-R antibodies treated horns.

Expression of OB-R, LIF-R, IL-1R tI and β3-Integrin by Mouse Endometrium

OB-R was mainly found in endometrial epithelial cells (lumen and glands) from non-pregnant mice (FIG. 12). After implantation occurred (Day 6 and 10 of pregnancy) OB-R staining was only detected in some epithelial glands. LPA-2 or LPA-2Sc treatments did not affect the expression of OB-R in vivo by mouse endometrium.

LPA-2 treatment negatively affected the levels of LIF-R (FIG. 13) and IL-1R tI (FIG. 14). By immunohistochemical analysis the β3-integrin was found mainly in EEC (lumen and glands) in pregnant (Day 6 and 10 of pregnancy) and non-pregnant mouse endometrium (FIG. 15). The intra-uterine injection of LPA-2 decreased the expression of β3-integrin by mouse endometrium (FIG. 15). No effect on β3-integrin staining was found in the uterine horns treated with LPA-2Sc or controls. Similar results on decrease of β3-integrin staining was found in mouse uterine horns treated with OB-R antibodies (data not shown).

Analysis data demonstrate that LPA-2 significantly decreased the expression of IL-1R tI, LIFR and β3 integrin at the expected time of embryo implantation in the mouse endometrium.

To substantiate an association of IL-1R or LIFR and integrin β3 in vivo, double-fluorescent confocal laser scanning microscopy on mouse endometrium was conducted. The cellular distribution and the relative intensity of fluorescence on the cells were assessed qualitatively. Immunofluorescence of Alexa fluor 593 for IL-1R and of Alexa Fluor 488 localizing anti-integrin β3 mAb revealed a strong membrane-associated granular pattern for each of the molecules. Using double-fluorescent labeling colocalization of IL-1R tI and integrin β3 in the same cells was indicated by yellow fluorescence. Similar results were found for the colocalization of LIFR and B3 integrin. However, LIFR showed higher immunofluorescence staining than IL-1R tI. The colocalization of both cytokine receptors by lacking proper combination of primary and secondary antibodies was not determined. The same problem was encountered in the double-fluorescent staining of either IL-1R, LIFR and OBR. This last receptor was detected with goat anti-mouse antibodies.

Materials and Methods

Chemicals

Armenian hamster antibody anti-β3 integrin (N-20, mouse origin), mouse anti-Armenian hamster IgGs, rabbit polyclonal antibodies again the carboxy terminus of LIF-R (C-19, human or mouse origin), IL-1 receptor type I (IL-1R tI, antibody M-20) and their respective blocking peptides for competition studies were obtained from Santa Cruz Biotechnology, Inc., Santa Cruz, Calif. Goat polyclonal anti-mouse OB-R (AF497, anti-NH2 terminal end of mouse OB-R), non-specific rabbit and goat IgGs were from R&D Systems Inc., MN. Other chemicals were obtained from Sigma Chemical Co., St. Louis, Mo. Normal goat and rabbit sera and biotinylated horse anti-mouse/anti-rabbit and rabbit anti-goat IgGs antibodies were from Vector Laboratories (Vector Laboratories, Burlingame, Calif.). Biotinylated goat anti rabbit IgGs antibodies (ALI3409, mouse IgG adsorbed) were obtained from BioSource International, Camarillo, Calif. Alexa Fluor 594 goat anti-rabbit IgG, Alexa Fluor 488 goat-anti mouse IgG and DAPI (4',6-diamino-2 phenylindole, dihydrochloride) were obtained from Molecular Probes Inc., Eugene, Oreg.

OB-R Inhibitors

LPA-2 and a scrambled version of this peptide (LPA-2Sc, negative control) were synthesized by solid-phase peptide synthesis and purified using high performance liquid chromatography (HPLC) as described elsewhere (Gonzalez and Leavis, *Endocrine* 21: 185-195 (2003)). LPA-1 (IQKVQD-DTKTLIKTIVTRINDISHTQSVSSKQ (MW: 3626.1454); SEQ ID NO:1) and a scrambled version of this peptide (LPA-1Sc, negative control) were similarly synthesized. The molecular masses of the peptides were determined by mass spectral analysis on a Voyager-RP Biospectrometer MALDI-TOF Workstation (Perseptive Biosystems, Cambridge, Mass.). Spectra were averages of approximately 200 scans. Dimethyl-sulphoxide (DMSO) was used as solvent for the preparation of stock solutions of LPA-1 and LPA-2 peptides. These solutions were diluted with phosphate-buffered saline (PBS) and sterile-filtered to produce the desired LPA-1 and LPA-2 working solutions for the in vivo experiments. The final DMSO concentration in the vehicle was 0.04%.

Goat anti-mouse OB-R antibodies and normal goat IgGs (negative control) from R & D Systems Inc. diluted in PBS were sterile filtered and also used to assess the impact of blockade of OB-R signaling on mouse implantation.

Animals

Virgin, 8-10 wk-old, female, C57BL6 mice (Charles River Laboratories, Wilmington, Mass.) were housed in the animal facilities at the Massachusetts General Hospital in accordance with NIH standards for the care and use of experimental animals. The room was provided with a controlled temperature range (22-24° C.) on a 14L:10D cycle. Mice were given water and food ad libitum.

Superovulation was induced in female mice (n=40) by an i.p. injection of 10 IU pregnant mare serum gonadotrophin (PMSG) (Sigma Chemical Company, St Louis, Mo.) followed by 10 IU hCG (Sigma) 48 h later. Next, the female mice were mated with fertile males of the same strain to induce pregnancy. The following morning, the females exhibiting vaginal copulatory plugs were separated for the next experiments. The day of vaginal plug was recorded as Day 1 of pregnancy. Mice were weighed before treatment and before they were euthanized.

Surgical Procedures and Intra-Uterine Blocking Treatments

Each mouse was labeled with an earring tag to record treatment and any observation pre or post treatment. Forty-eight hours after hCG administration (Day 3 of pregnancy), female mice with documentation of vaginal plug were anaesthetized by i.p injection of Avertin (2,2,2 tribromoethanol, 30 μl/g body weigh; Sigma). A surgical incision was made on the dorsal mid-line through the skin, and each uterine horn with fat pad and ovary was pulled-out of the body cavity using forceps (Roboz, Gainthersburg, Md.). Under a dissecting microscope (Cambridge Laboratories) different compounds were injected in each uterine horn. Each compound was delivered slowly using a Hamilton syringe (Hamilton Co., model PC010) holding an in-house made glass needle (<27 G; capillary pipette 20 μl, Unopette, Becton Dickinson). The glass needle allowed us to observe that the compounds were effectively injected into each horn. The surgical incision was closed with metal auto clips (9 mm, Becton Dickinson). Mice were placed in warmed cage (slide warmer, Fisher) and returned to the animal facilities after full recovery from the anesthetic.

On Day 3 of pregnancy, 15 μl of LPA-2 or LPA-2Sc (3.3 μM) or 10 μl of LPA-1 or LPA-1Sc (3.3 μM) were delivered into the lumen of the proximal region of the right horn of each pregnant mouse (n=15). Each animal served as it own internal control, with the left uterine horn receiving the vehicle. For positive control, a group of mice received 15 μl goat anti OB-R antibodies at doses of 1.5 and 7.5 μg in the right horn and non-specific goat IgG solutions in the left horn. Concentrations of OB-R inhibitors used in vivo were calculated from results of previous experiments in endometrial cell cultures [Gonzalez and Leavis, *Endocrine* 21: 185-195 (2003)]. The effects of surgical treatment, intra-uterine injection and toxicity of vehicle solutions on implantation were also assessed in 8 pregnant mice that received intra-uterine injections of PBS and PBS-DMSO.

To analyze the effects of OB-R inhibitors on pregnancy and expression of several molecules by the endometrium the mice were euthanized by cervical dislocation on Day 6 and 10 of pregnancy.

On Day 6 of pregnancy the mice received an intra-ocular injection of 0.1 ml of 1% Evans Blue dye in saline 5 min before euthanasia on the morning of day 6 after mating. Uteri from these mice were examined for implantation sites by observing a localized increase of uterine vascular permeability (Paria et al., 2001). The uteri were extracted and the implantation sites were counted in each horn. On The numbers of implanted embryos in the right (experimental) and left (control) uterine horns were counted under a dissecting microscope. Uteri without blue bands from 6-day pregnant mice were flushed to recover unimplanted blastocysts. The uteri from 10-day pregnant mice were examined with the naked eye for implantation masses. The histology of uteri with decidual capsules (implantation site) were examined for evidence of embryological development. A portion of each uterine horn was dissected and treated to produce cryostat sections or fixed in 4% paraformaldehyde in PBS and embedded to produce paraffin blocks.

Immunohistochemical Determinations

To assess the potential effects of blockade of endometrial OB-R function in vivo on the expression of various cytokine receptors, immunohistochemistry in cryostat and paraffin block sections (4 μm) was performed. Unmasking of several antigen epitopes (β3-integrin, LIF-R and IL-1R tI) in paraffin sections was performed. Briefly, samples were boiled for 10 min in a pressure cooker containing 10 mM sodium citrate/1 mM ethylene-diamino tetracetic acid (EDTA), pH 6 solution. After quenching endogenous peroxidase activity with $H_2O_2$ (3% water solution) and blocking (2.5% horse or rabbit normal serum), tissue sections were incubated for 1 h at room temperature with the following primary antibodies diluted in PBS-0.1% BSA: anti-β3 integrin, IL-1R tI, LIF-R and OB-R antibodies (all at 4 μg/ml). Biotinylated secondary antibodies anti-primary antibody specie were used. The tissues were incubated with a streptavidin-biotin-peroxidase system according to the manufacturer's directions (Vectastain, ABC-AP kit, Vector Laboratories, Burlingame, Calif.), counterstained with hematoxylin (Dako Corporation, Carpinteria, Calif.) and mounting with VectaMount (Vector Labs) for permanently preserve staining from the precipitable enzyme substrate. Negative controls included tissue preparations in which the primary antibodies were substituted by irrelevant species matched IgGs. Negative controls for competitive studies with anti IL-1R tI and LIF-R antibodies were generated by pre-incubation with their respective blocking peptides (20 μg/ml, Santa Cruz Biotechnology). All washing steps were performed by immersion of the preparations 3 time in PBS for 5 min at room temperature.

Results from immunohistochemistry were analyzed blind by a single examiner. In addition, a limited number of immunohistochemical preparations were examined twice by the same observer or by an additional observer. The number of endometrial stromal and epithelial cells (glands or lumen) positively stained (from a total number of 100 cells) for each antigen and preparation were recorded in representative fields selected in a random manner. Staining intensity was assigned using a semiquantitative HSCORE as was described by Lessey et al (Lessey et al., *J. Clin. Invest.* 90:188-195 (1992)). The HSCORE was calculated using the following equation: HSCORE=ΣPi(i+1), where "i" is the intensity of staining within a value of 1, 2 or 3 (weak, moderate and strong, respectively) and "Pi" is the percentage of stained cells for each intensity varying from 0 to 100% (Lessey et al., *J. Clin. Invest* 90: 188-195 (1992)).

Confocal Laser Scanning Microscopy

Confocal laser scanning microscopy was performed in serial sections from paraffin blocks to determine the colocalization of receptors (OB-R, IL-1R tI and LIF-R) and β3 integrin within endometrium tissue from non-pregnant and pregnant mice after intra-uterine treatments. The protocols for immunostaining used were similar to those already described for regular color-based immunohistochemistry but the secondary antibodies and counterstaining agent were changed. Alexa Fluor 594 goat anti-rabbit IgG (red fluorescence) and Alexa Fluor 488 goat-anti mouse IgG (green fluorescence) conjugates were used to detect LIF-R and IL-1R tI, and β3 integrin, respectively. In addition, a second FITC-conjugated antibody (rabbit anti-goat IgG-FITC) was used to detect OB-R. The double-fluorescent stained specimens were analyzed with a confocal laser scanning microscope equipped with an external argon laser (BioRad). To avoid photobleaching of fluorochromes during fluorescence microscopy, the slides were embedded in anti-fade solution (Dako). For nuclear and chromosome counterstaining a 300 nM DAPI PBS-dimethylformamide (DMF) solution was used.

The invention claimed is:

1. A method for reducing or inhibiting ObR signaling in a leptin-responsive cell, the method comprising administering to a mammal a therapeutically effective amount of a peptide consisting of SEQ ID NO: 1.

2. The method of claim 1 wherein the mammal is selected from the group consisting of humans, mice, and rabbits.

3. The method of claim 1 wherein the administration of the peptide results in the reduction of the likelihood of embryo implantation.

4. The method of claim 1 wherein the reduction or inhibition of ObR signaling in the cell results in a reduction or inhibition of the up-regulatory effects of leptin on a signaling event downstream of ObR.

5. The method of claim 4 wherein the signaling event downstream of the leptin receptor consists of p-Stat-3, β3-integrin, IL-1 and LIF signaling.

6. The method of claim 1 wherein the reduction or inhibition of ObR signaling results in a reduction or inhibition of the up-regulatory effects of leptin on the expression of a leptin-sensitive target.

7. The method of claim 6 wherein the leptin-sensitive target is selected from the group consisting of p-Stat-3, β3-integrin, IL-1R tI, LIF-R, LIF, IL-1β, and IL-1Ra.

* * * * *